(12) United States Patent
Glicksman

(10) Patent No.: US 9,370,414 B2
(45) Date of Patent: Jun. 21, 2016

(54) RECONSTRUCTIVE BREAST PROSTHESES

(75) Inventor: Avraham Glicksman, Petach Tikva (IL)

(73) Assignee: IMPLITE LTD., Petach Tikva (IL)

( * ) Notice: Subject to any disclaimer, the term of this patent is extended or adjusted under 35 U.S.C. 154(b) by 65 days.

(21) Appl. No.: 13/126,588

(22) PCT Filed: Oct. 27, 2009

(86) PCT No.: PCT/IL2009/001001
§ 371 (c)(1),
(2), (4) Date: Apr. 28, 2011

(87) PCT Pub. No.: WO2010/049926
PCT Pub. Date: May 6, 2010

(65) Prior Publication Data
US 2011/0208302 A1   Aug. 25, 2011

Related U.S. Application Data

(60) Provisional application No. 61/197,613, filed on Oct. 28, 2008, provisional application No. 61/160,370, filed on Mar. 16, 2009.

(51) Int. Cl.
*A61F 2/02* (2006.01)
*A61F 2/12* (2006.01)

(52) U.S. Cl.
CPC ........................................ *A61F 2/12* (2013.01)

(58) Field of Classification Search
USPC ................................. 623/7, 8, 23.74; 156/145
See application file for complete search history.

(56) References Cited

U.S. PATENT DOCUMENTS

| | | |
|---|---|---|
| 3,366,975 A | 2/1968 | Paisgman |
| 3,683,424 A | 8/1972 | Pangman |
| 3,934,274 A | 1/1976 | Hartley, Jr. |
| 3,986,213 A | 10/1976 | Lynch |
| 4,178,643 A | 12/1979 | Cox, Jr. |
| 4,298,998 A | 11/1981 | Naficy |
| 4,430,764 A | 2/1984 | Finkelstein |
| 4,507,810 A | 4/1985 | Bartholdson |
| 4,624,671 A | 11/1986 | Kress |
| 4,650,487 A | 3/1987 | Chaglassian |
| 4,651,717 A | 3/1987 | Jakubczak |
| 4,685,447 A | 8/1987 | Iversen et al. |
| 4,773,908 A | 9/1988 | Becker |
| 4,773,909 A | 9/1988 | Chaglassian |
| 4,790,848 A | 12/1988 | Cronin |

(Continued)

FOREIGN PATENT DOCUMENTS

| | | |
|---|---|---|
| EP | 0054359 | 6/1982 |
| EP | 1820473 | 8/2007 |

(Continued)

*Primary Examiner* — Yashita Sharma
(74) *Attorney, Agent, or Firm* — The Roy Gross Law Firm, LLC; Roy Gross

(57) ABSTRACT

A reconstructive breast prosthesis suitable for implantation into a void in a breast following a lumpectomy procedure in which a body of tissue is excised from the breast, the reconstructive breast prosthesis including an implant body at least generally configured to assume an implant shape corresponding to the shape of the body of tissue excised from the breast and an implant shape retaining structure adapted to maintain the implant body in the implant shape, the reconstructive breast prosthesis having an overall density which is less than the density of the body of tissue excised from the breast.

16 Claims, 26 Drawing Sheets

(56) References Cited

U.S. PATENT DOCUMENTS

| | | | |
|---|---|---|---|
| 4,944,749 | A | 7/1990 | Becker |
| 5,060,328 | A | 10/1991 | Larson |
| 5,074,878 | A | 12/1991 | Bark et al. |
| 5,092,882 | A | 3/1992 | Lynn |
| 5,104,409 | A * | 4/1992 | Baker .............. 623/8 |
| 5,110,653 | A | 5/1992 | Landi |
| 5,122,405 | A | 6/1992 | Landi |
| 5,137,769 | A | 8/1992 | Landi |
| 5,159,725 | A | 11/1992 | Larson |
| 5,180,619 | A | 1/1993 | Landi et al. |
| 5,203,607 | A | 4/1993 | Landi |
| 5,236,454 | A | 8/1993 | Miller |
| 5,246,454 | A | 9/1993 | Peterson |
| 5,340,352 | A | 8/1994 | Nakanishi et al. |
| 5,358,521 | A | 10/1994 | Shane |
| 5,376,117 | A | 12/1994 | Pinchuk |
| 5,437,824 | A | 8/1995 | Carlisle |
| 5,496,367 | A | 3/1996 | Fisher |
| 5,496,610 | A | 3/1996 | Landi et al. |
| 5,500,019 | A | 3/1996 | Johnson |
| 5,509,484 | A | 4/1996 | Landi et al. |
| 5,534,343 | A | 7/1996 | Landi et al. |
| 5,545,217 | A | 8/1996 | Offray et al. |
| 5,617,595 | A | 4/1997 | Landi et al. |
| 5,658,330 | A | 8/1997 | Carlisle |
| 5,701,621 | A | 12/1997 | Landi et al. |
| 5,824,081 | A | 10/1998 | Knapp et al. |
| 5,836,871 | A | 11/1998 | Wallace et al. |
| 5,840,397 | A | 11/1998 | Landi et al. |
| 5,840,400 | A | 11/1998 | Landi et al. |
| 5,902,335 | A | 5/1999 | Snyder, Jr. |
| 5,961,552 | A | 10/1999 | Iversen et al. |
| 6,066,220 | A * | 5/2000 | Schneider-Nieskens ..... 156/145 |
| 6,183,514 | B1 | 2/2001 | Becker |
| 6,187,043 | B1 | 2/2001 | Ledergerber |
| 6,206,930 | B1 | 3/2001 | Burg et al. |
| 6,214,045 | B1 * | 4/2001 | Corbitt et al. ................. 623/8 |
| 6,228,116 | B1 | 5/2001 | Ledergerber |
| 6,315,796 | B1 | 11/2001 | Eaton |
| 6,415,583 | B1 | 7/2002 | Landi et al. |
| 6,432,138 | B1 | 8/2002 | Offray et al. |
| 6,544,287 | B1 * | 4/2003 | Johnson et al. ................. 623/7 |
| 6,605,116 | B2 | 8/2003 | Falcon et al. |
| 6,802,861 | B1 | 10/2004 | Hamas |
| 6,811,570 | B1 | 11/2004 | Gehl |
| 6,875,233 | B1 | 4/2005 | Matthew Lamar Turner |
| 6,932,840 | B1 | 8/2005 | Bretz |
| 8,236,054 | B2 | 8/2012 | Purkait |
| 8,545,557 | B2 | 10/2013 | Glicksman et al. |
| 2001/0010024 | A1 | 7/2001 | Ledergerber |
| 2002/0038147 | A1 | 3/2002 | Miller, III |
| 2002/0143396 | A1 | 10/2002 | Falcon et al. |
| 2003/0040806 | A1 | 2/2003 | MacDonald |
| 2003/0074084 | A1 | 4/2003 | Nakao |
| 2003/0149481 | A1 | 8/2003 | Guest et al. |
| 2004/0148024 | A1 | 7/2004 | Williams |
| 2004/0153151 | A1* | 8/2004 | Gonzales de Vicente ........ 623/8 |
| 2004/0162613 | A1 | 8/2004 | Roballey |
| 2004/0176841 | A1* | 9/2004 | Ferguson .................... 623/7 |
| 2006/0264399 | A1 | 11/2006 | Lim et al. |
| 2006/0282164 | A1 | 12/2006 | Seastrom |
| 2007/0299541 | A1 | 12/2007 | Chernomorsky et al. |
| 2008/0221679 | A1 | 9/2008 | Hamas |
| 2009/0093878 | A1 | 4/2009 | Glicksman |
| 2009/0299473 | A1* | 12/2009 | Govrin-Yehudian et al. .... 623/8 |
| 2010/0114311 | A1 | 5/2010 | Becker |
| 2011/0054606 | A1 | 3/2011 | Forsell |
| 2011/0288639 | A1 | 11/2011 | Trilokekar |
| 2012/0078366 | A1 | 3/2012 | Jones |
| 2012/0165934 | A1 | 6/2012 | Schuessler |
| 2012/0226352 | A1 | 9/2012 | Becker |

FOREIGN PATENT DOCUMENTS

| | | |
|---|---|---|
| EP | 1510189 | 4/2008 |
| EP | 2387971 A1 | 11/2011 |
| FR | 2 859 098 A1 | 3/2005 |
| FR | 2 862 523 A1 | 5/2005 |
| JP | 58-15612 A | 1/1983 |
| JP | S5815612 | 1/1983 |
| JP | 11-503652 A | 3/1999 |
| JP | 2001-519203 A | 10/2001 |
| JP | 2004-130118 A | 4/2004 |
| JP | 2005-137398 A | 6/2005 |
| RU | 02332188 | 8/2008 |
| WO | 98/10803 | 3/1998 |
| WO | 99/20319 | 4/1999 |
| WO | 01/66039 A1 | 9/2001 |
| WO | 2006/114786 | 11/2006 |
| WO | 2007/000756 | 1/2007 |
| WO | 2008/038851 | 4/2008 |
| WO | 2008/081439 A2 | 7/2008 |
| WO | 2010/049926 | 5/2010 |
| WO | 2011081826 | 7/2011 |
| WO | 2011086537 | 7/2011 |

* cited by examiner

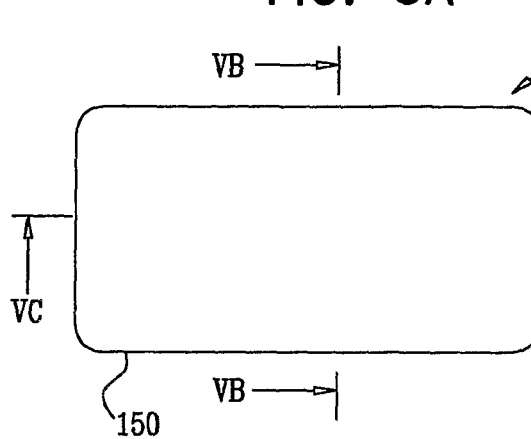
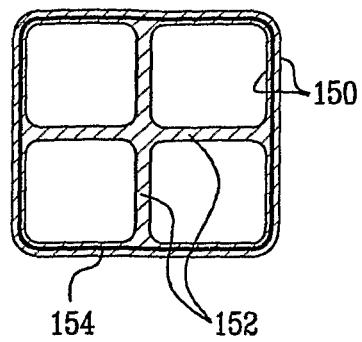
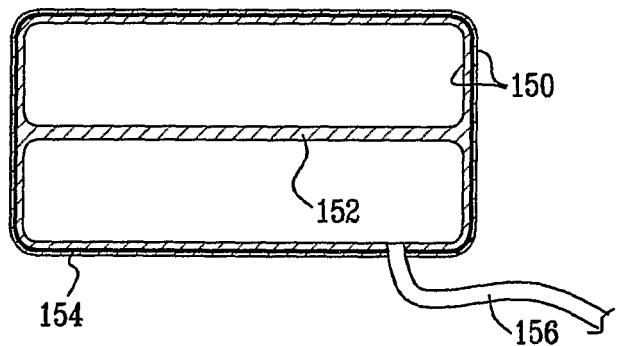
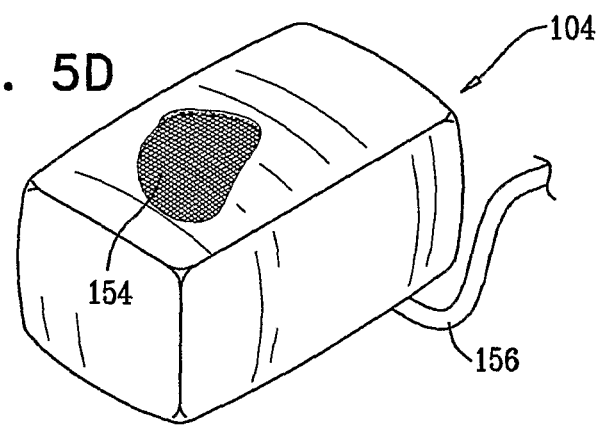

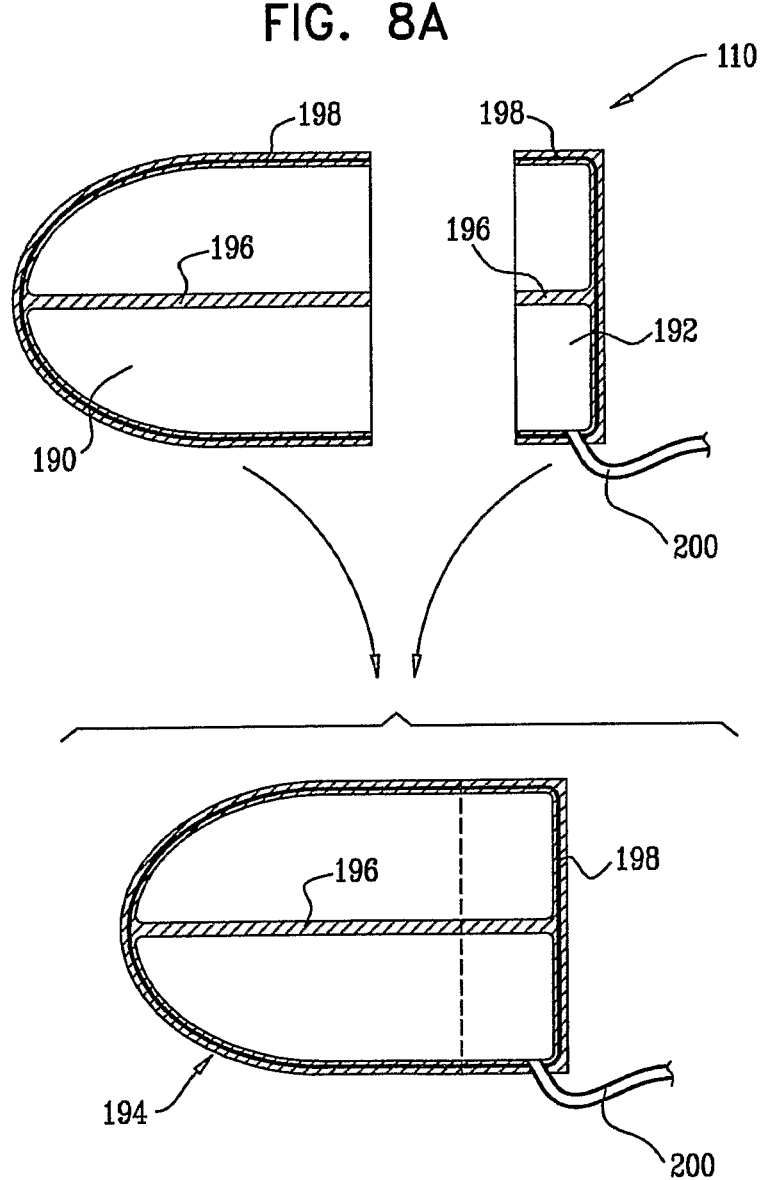

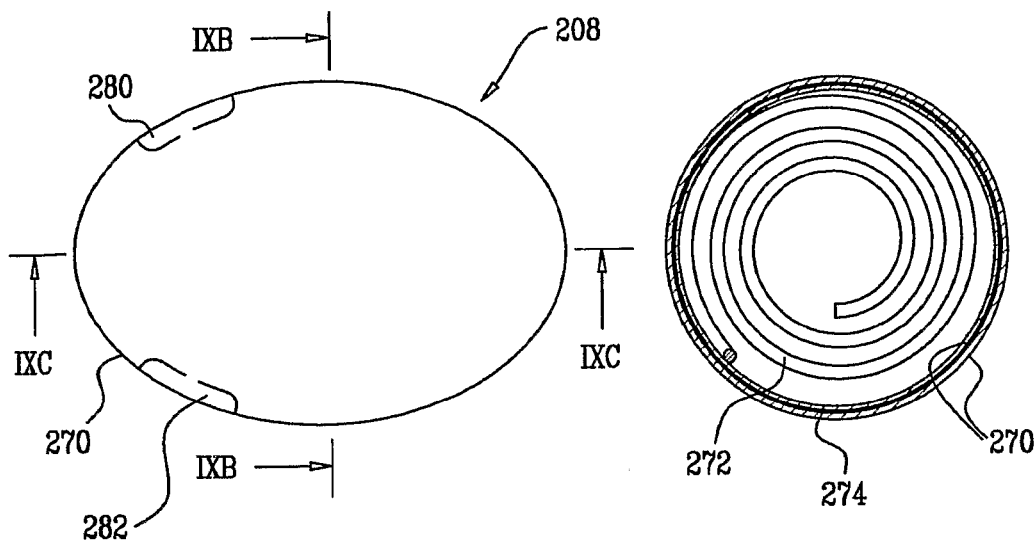
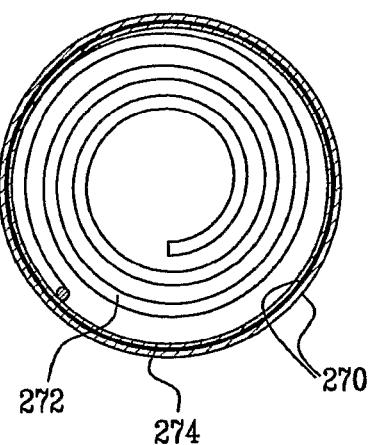
FIG. 9A
FIG. 9B
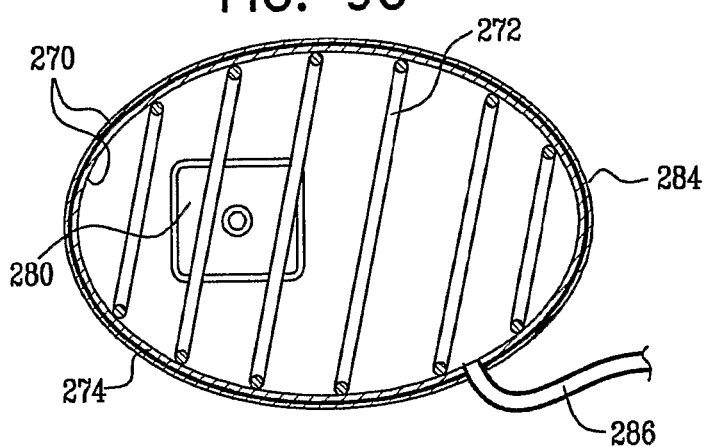
FIG. 9C
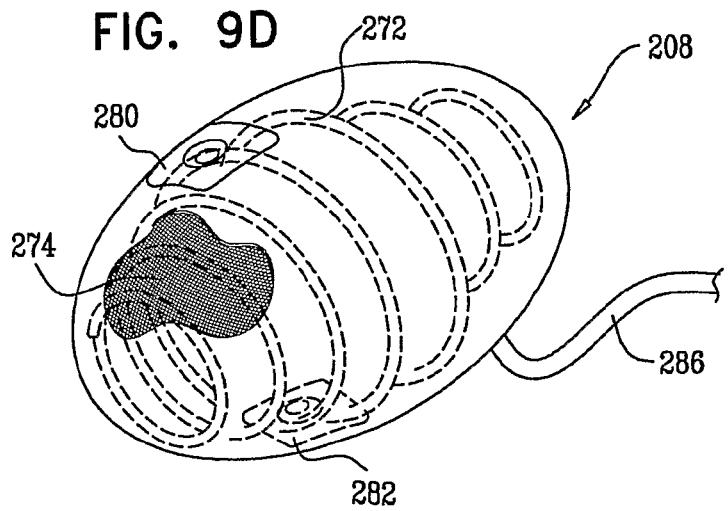
FIG. 9D

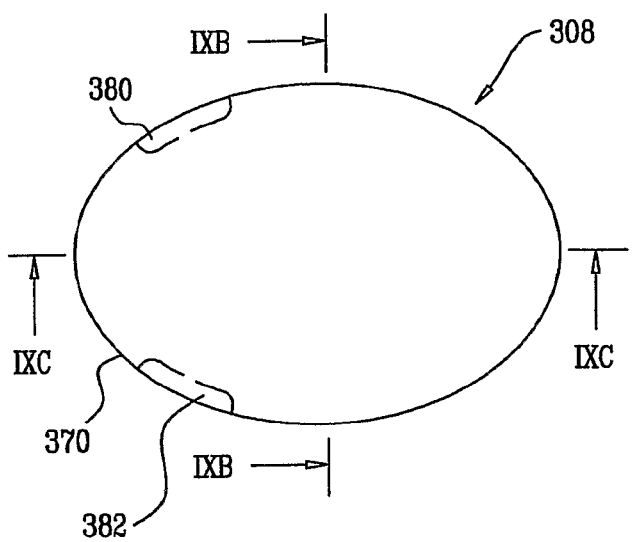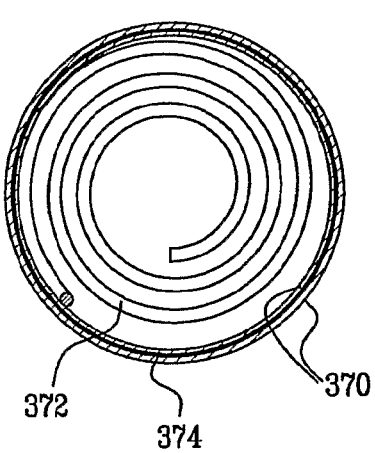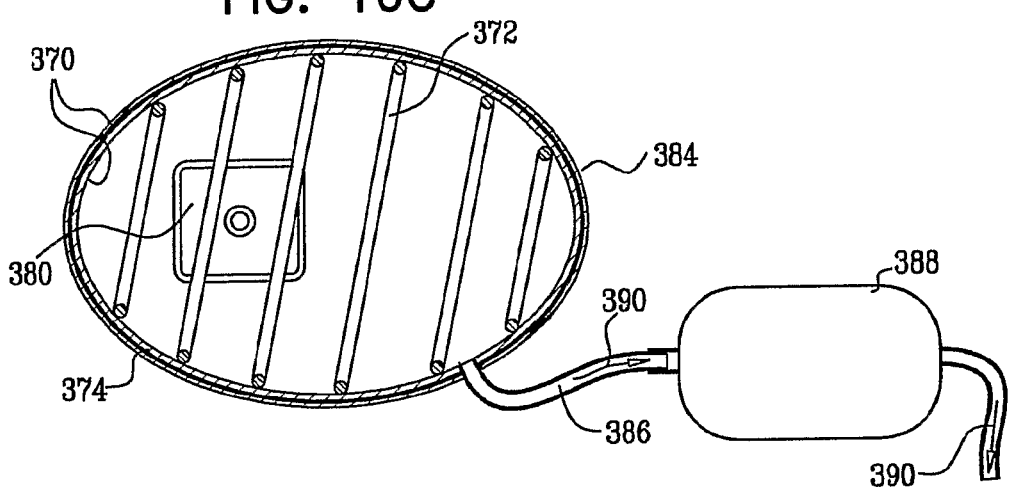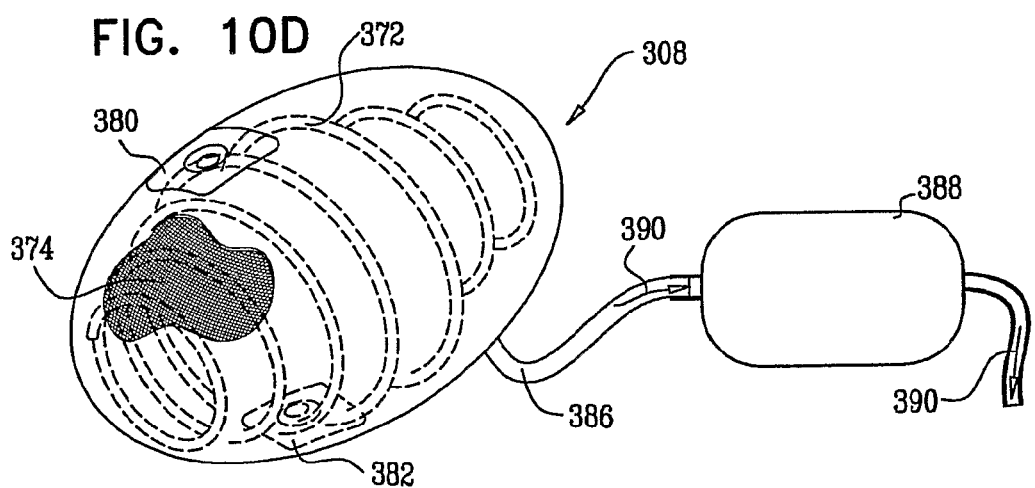

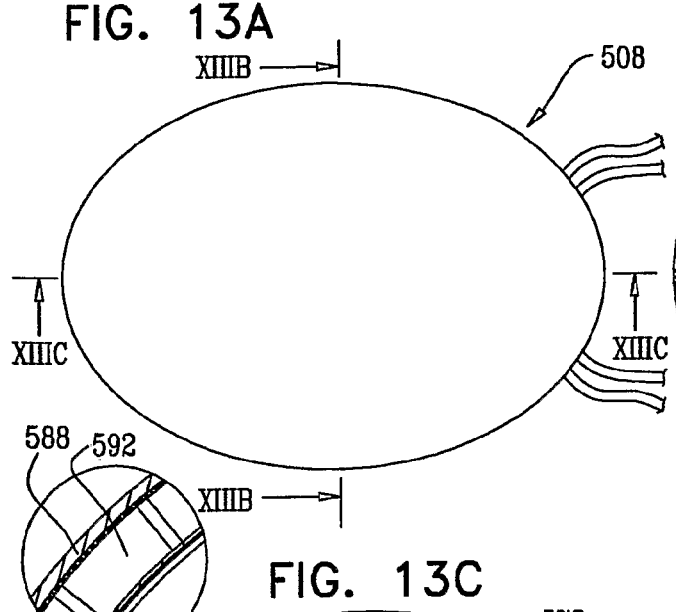
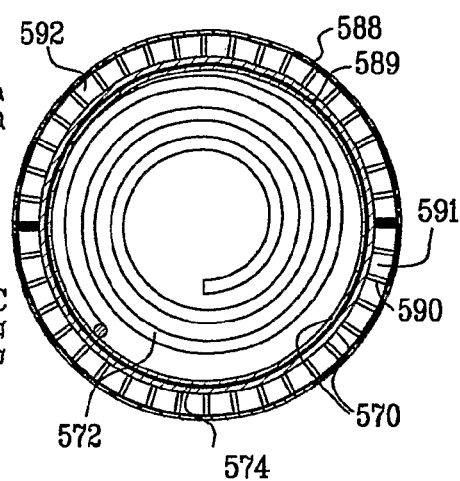
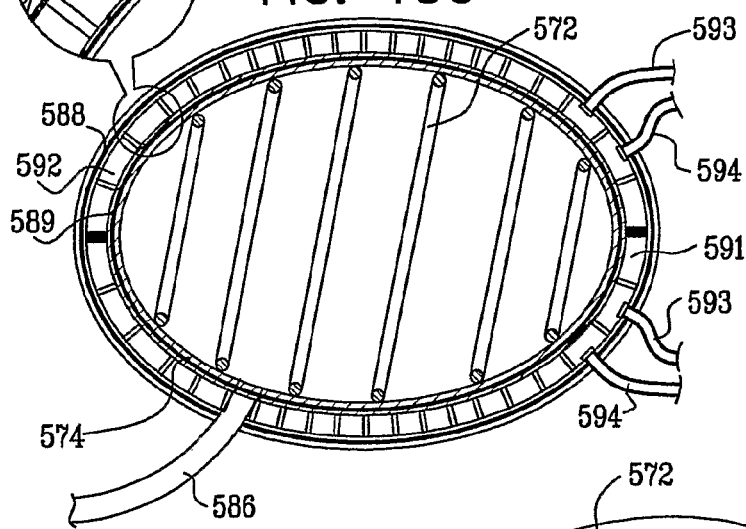
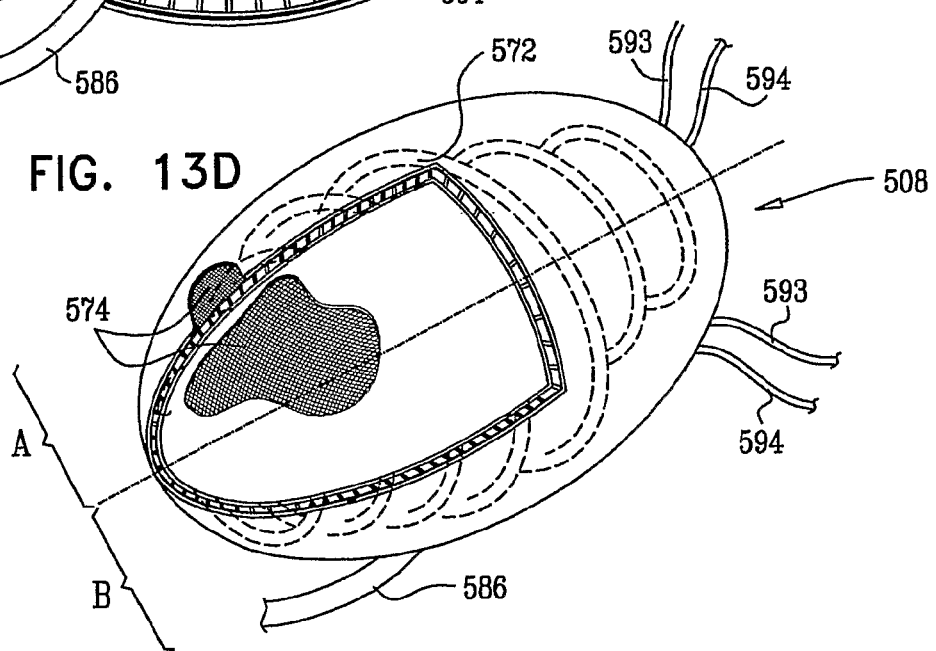

RECONSTRUCTIVE BREAST PROSTHESES

REFERENCE TO RELATED APPLICATIONS

Reference is made to applicant's U.S. Provisional Patent Application Ser. No. 61/197,613 filed Oct. 28, 2008 and entitled Lumpectomy Implant, the disclosure of which is hereby incorporated by reference and priority of which is hereby claimed pursuant to 37 CFR 1.78(a) (4) and (5)(i).

Reference is made to applicant's U.S. Provisional Patent Application Ser. No. 61/160,370 filed Mar. 16, 2009 and entitled Lumpectomy Implant, the disclosure of which is hereby incorporated by reference and priority of which is hereby claimed pursuant to 37 CFR 1.78(a) (4) and (5)(i).

Reference is made to applicants' copending PCT Application No. PCT/IL2007/001629 filed Dec. 31, 2007, the disclosure of which is hereby incorporated by reference.

Reference is made to applicants' copending U.S. patent application Ser. No. 11/918,861 filed Oct. 19, 2007, the disclosure of which is hereby incorporated by reference.

FIELD OF THE INVENTION

The present invention relates generally to reconstructive breast prostheses.

BACKGROUND OF THE INVENTION

The following U.S. Patent publications are believed to represent the current state of the art:
U.S. Pat. Nos. 6,214,045 and 5,824,081; and
U.S. Published Patent Application 2006/0282164.

SUMMARY OF THE INVENTION

The present invention seeks to provide improved reconstructive breast prostheses and methods for implantation thereof.

There is thus provided in accordance with a preferred embodiment of the present invention a reconstructive breast prosthesis suitable for implantation into a void in a breast following a lumpectomy procedure in which a body of tissue is excised from the breast, the reconstructive breast prosthesis including an implant body at least generally configured to assume an implant shape corresponding to the shape of the body of tissue excised from the breast and an implant shape retaining structure adapted to maintain the implant body in the implant shape, the reconstructive breast prosthesis having an overall density which is less than the density of the body of tissue excised from the breast.

There is also provided in accordance with another preferred embodiment of the present invention a reconstructive breast prosthesis suitable for implantation into a void in a breast following a lumpectomy procedure in which a body of tissue is excised from the breast, the reconstructive breast prosthesis including an implant body at least generally configured to assume an implant shape corresponding to the shape of the body of tissue excised from the breast and an implant shape retaining structure adapted to maintain the implant body in the implant shape, the reconstructive breast prosthesis having an overall density which is less than the density of the remaining tissue of the breast surrounding the implant body There is further provided in accordance with yet another preferred embodiment of the present invention a reconstructive breast prosthesis suitable for implantation into a void in a breast following a lumpectomy procedure in which a body of tissue is excised from the breast, the reconstructive breast prosthesis including an implant body at least generally configured to assume an implant shape corresponding to the shape of the body of tissue excised from the breast and an implant shape retaining structure adapted to maintain the implant body in the implant shape, the reconstructive breast prosthesis having an overall density which is less than 0.5 grams/cc.

There is yet further provided in accordance with still another preferred embodiment of the present invention a reconstructive breast prosthesis suitable for implantation into a void in a breast following a lumpectomy procedure in which a body of tissue is excised from the breast, the reconstructive breast prosthesis including a selectably sizable implant body and a cap portion operative to be sealed to the selectably sizable implant body, the implant being generally configurable to assume an implant shape corresponding to the shape of the body of tissue excised from the breast.

There is still further provided in accordance with another preferred embodiment of the present invention a reconstructive breast prosthesis facilitating temporary therapeutic radiation treatment suitable for reconstructive implantation into a void in a breast immediately following a procedure in which a body of tissue is excised from the breast and prior to radiation therapy, the reconstructive breast prosthesis including a body generally configured to assume the shape of a reconstructive prosthesis corresponding to the shape of the body of tissue excised from the breast, at least one radioactive material receiving volume formed in the body and at least one conduit communicating with the at least one radioactive material receiving volume and adapted for providing at least ingress of radioactive material thereto.

Preferably, the implant body is a lumpectomy implant body.

There is yet further provided in accordance with still another preferred embodiment of the present invention a reconstructive breast prosthesis facilitating temporary therapeutic treatment suitable for reconstructive implantation into a void in a breast immediately following a lumpectomy procedure in which a body of tissue is excised from the breast, the reconstructive breast prosthesis including a body generally configured to assume the shape of a reconstructive prosthesis corresponding to the shape of the body of tissue excised from the breast, at least one therapeutic substance receiving volume formed in the body and at least one conduit communicating with the at least one therapeutic substance receiving volume and adapted for providing dispensing of the therapeutic substance from the therapeutic substance receiving volume to surrounding tissue.

Preferably, the reconstructive breast prosthesis includes at least one pump in fluid communication with an interior of the implant body for providing dispensing of the therapeutic substance from the therapeutic substance receiving volume to surrounding tissue.

Preferably, the reconstructive breast prosthesis has a specific gravity which is less than 0.9 gm/cm3.

More preferably, the reconstructive breast prosthesis has a specific gravity which is less than 0.5 gm/cm3.

Preferably, the implant body is formed of a resilient biocompatible material.

Preferably, the reconstructive breast prosthesis includes an implant shape retaining structure adapted to maintain the implant body in the implant shape.

In accordance with a preferred embodiment of the present invention the implant shape retaining structure includes at least one rib. Alternatively, the implant shape retaining structure includes at least one spring. Additionally or alternatively, the implant shape retaining structure includes at least one mesh.

In accordance with a preferred embodiment of the present invention the reconstructive breast prosthesis has at least one tube which is in communication with an interior of the implant body. Preferably, the implant body includes at least two mutually sealed portions. Additionally, the at least one tube includes at least two tubes, each communicating with one of the at least two mutually sealed portions. Additionally, at least one of the at least two tubes is selectably detachable from a corresponding one of the at least two mutually sealed portions.

In accordance with a preferred embodiment of the present invention the reconstructive breast prosthesis includes at least one valve governing communication between at least one of the at least two tubes and a corresponding at least one of the at least two mutually sealed portions.

Preferably, the reconstructive breast prosthesis includes at least one pump in fluid communication with an interior of the implant body.

Preferably, the reconstructive breast prosthesis includes at least one injection port. Additionally, the at least one injection port includes first and second mutually opposed injection ports.

There is also provided in accordance with another preferred embodiment of the present invention a method for implantation of a reconstructive breast prosthesis into a void in a breast following a lumpectomy procedure in which a body of tissue is excised from the breast through an incision, the method including inserting the reconstructive breast prosthesis into the void, the reconstructive breast prosthesis including an implant body at least generally configured to assume an implant shape corresponding to the shape of the body of tissue excised from the breast and an implant shape retaining structure adapted to maintain the implant body in the implant shape, the reconstructive breast prosthesis having an overall density which is less than the density of the body of tissue excised from the breast, and closing the incision.

There is further provided in accordance with still another preferred embodiment of the present invention a method for implantation of a reconstructive breast prosthesis into a void in a breast following a lumpectomy procedure in which a body of tissue is excised from the breast through an incision, the method including inserting the reconstructive breast prosthesis into the void, the reconstructive breast prosthesis including an implant body at least generally configured to assume an implant shape corresponding to the shape of the body of tissue excised from the breast and an implant shape retaining structure adapted to maintain the implant body in the implant shape, the reconstructive breast prosthesis having an overall density which is less than the density of the remaining tissue of the breast surrounding the implant body, and closing the incision.

There is yet further provided in accordance with even a further preferred embodiment of the present invention a method for implantation of a reconstructive breast prosthesis into a void in a breast following a lumpectomy procedure in which a body of tissue is excised from the breast through an incision, the method including providing a reconstructive breast prosthesis including a selectably sizable implant body and a cap portion, cutting the selectably sizable implant body to a desired size, sealing the cap portion to the selectably sizable implant body thereby providing a selectably sized implant, inserting the selectably sized implant into the void and closing the incision.

There is still further provided in accordance with yet another preferred embodiment of the present invention a method for implantation of a reconstructive breast prosthesis into a void in a breast following a procedure in which a body of tissue is excised from the breast through an incision, the method including providing a reconstructive breast prosthesis facilitating temporary therapeutic radiation treatment suitable for reconstructive implantation into a void in a breast, the reconstructive breast prosthesis including a body generally configured to assume the shape of a reconstructive prosthesis corresponding to the shape of the body of tissue excised from the breast, at least one radioactive material receiving volume formed in the body and at least one conduit communicating with the at least one radioactive material receiving volume and adapted for providing at least ingress of radioactive material thereto, supplying at least one radioactive material to the at least one radioactive material receiving volume, retaining the at least one radioactive material in the at least one radioactive material receiving volume for at least one treatment duration; and removing the at least one radioactive material from the at least one radioactive material receiving volume following the at least one treatment duration.

In accordance with a preferred embodiment of the present invention the radioactive material is in a solid form. Alternatively the radioactive material is in a liquid form.

Preferably the radioactive material is inserted and removed via the at least two tubes.

Preferably the at least one radioactive material receiving volume includes at least two mutually sealed portions and different radioactive substances are inserted into different ones of the at least two mutually sealed portions.

Preferably the at least one radioactive material receiving volume includes at least two mutually sealed portions and different concentrations of a radioactive substance are inserted into different ones of the at least two mutually sealed portions.

There is still further provided in accordance with yet another preferred embodiment of the present invention a method for implantation of a reconstructive breast prosthesis into a void in a breast following a procedure in which a body of tissue is excised from the breast through an incision, the method including providing a reconstructive breast prosthesis facilitating temporary therapeutic treatment suitable for reconstructive implantation into a void in a breast immediately following a lumpectomy procedure in which a body of tissue is excised from the breast, the reconstructive breast prosthesis including a body generally configured to assume the shape of a reconstructive prosthesis corresponding to the shape of the body of tissue excised from the breast, at least one therapeutic substance receiving volume formed in the body and at least one conduit communicating with the at least one therapeutic substance receiving volume and adapted for providing dispensing of the therapeutic substance from the therapeutic substance receiving volume, to surrounding tissue and dispensing the therapeutic substance from the therapeutic substance receiving volume to surrounding tissue.

In accordance with a preferred embodiment of the present invention the method also includes attaching a pump to the reconstructive breast prosthesis. Additionally, the method also includes dispensing a fluid from the implant through the pump.

Preferably, the method also includes injecting a fluid into the reconstructive breast prosthesis. Additionally or alternatively, the method also includes removing a fluid from the interior of the reconstructive breast prosthesis. In accordance with a preferred embodiment of the present invention the fluid is air.

In accordance with a preferred embodiment of the present invention the fluid includes a therapeutic liquid. Additionally, the therapeutic liquid includes a combination of a solvent and at least one of a drug, chemical compound and radioactive material.

Preferably, the fluid is permeable through an outer wall of the implant.

BRIEF DESCRIPTION OF THE DRAWINGS

The present invention will be understood and appreciated more fully from the following detailed description, taken in conjunction with the drawings in which.

Figure 8B:
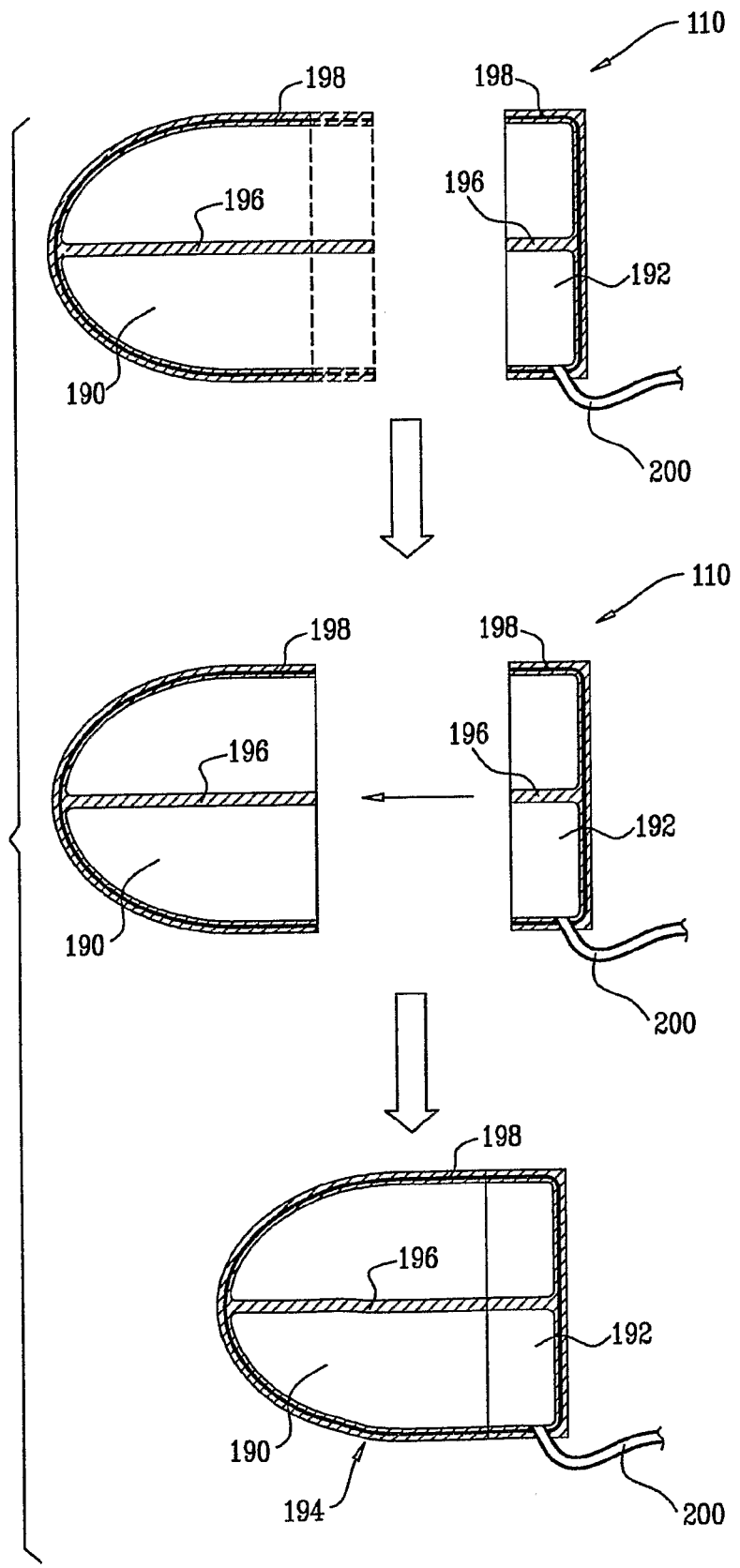
Figure 11:
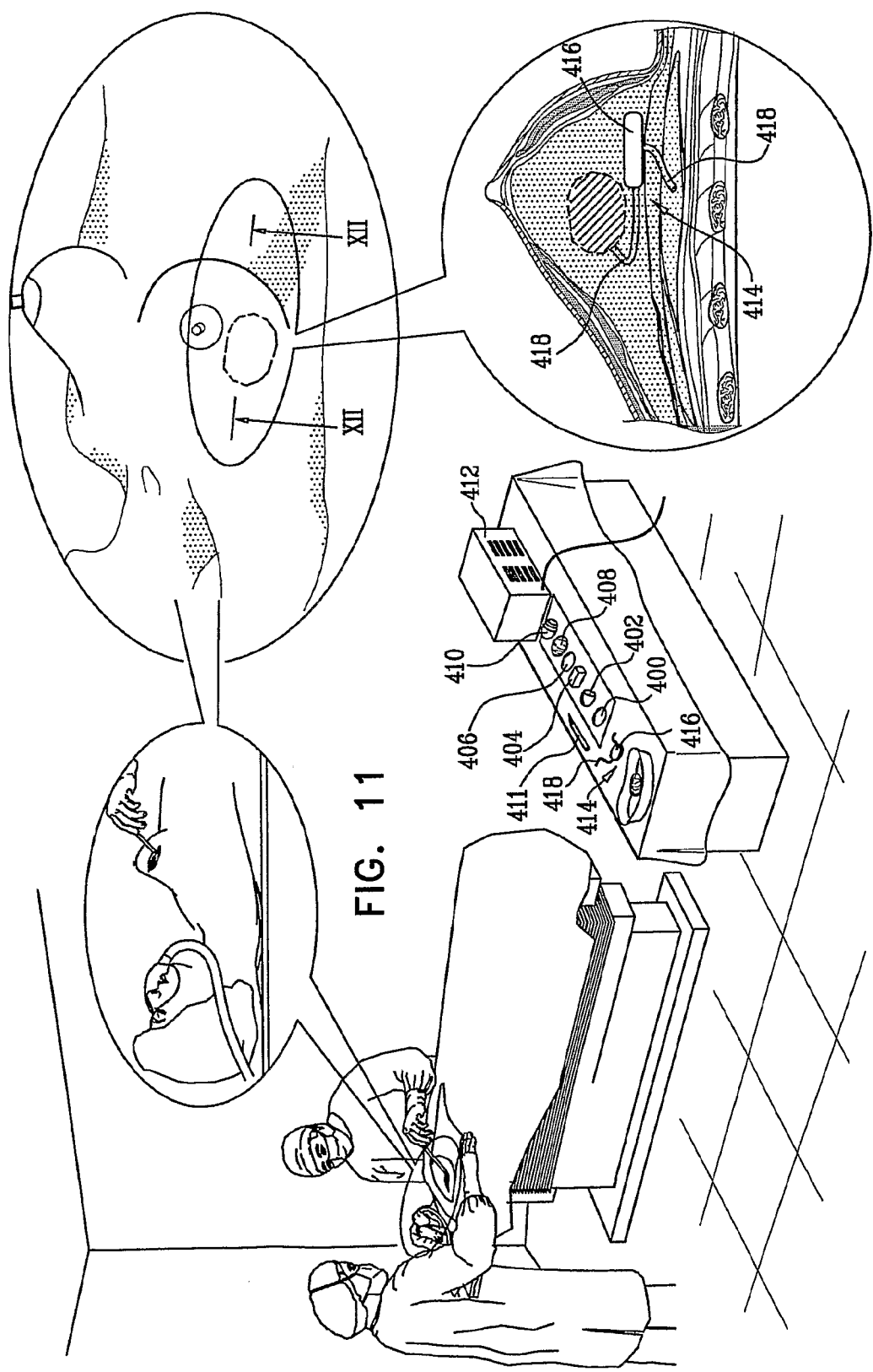

FIGS. $5A_5$, 5B, 5C and 5D are respective simplified pictorial, cross sectional, longitudinal sectional and partially cut away side view illustrations of a reconstructive breast prosthesis constructed and operative in accordance with still mother embodiment of the present invention;

FIGS. 6A, 6B, 6C and 6D are respective simplified pictorial, cross sectional, longitudinal sectional and partially cut away side view illustrations of a*econstructive breast prosthesis constructed and operative in accordance with yet mother embodiment of the present invention;

FIGS. 7A, 7B, 7C and 7D are respective simplified pictorial, cross sectional, longitudinal sectional and partially cut away side view illustrations of a reconstructive breast prosthesis constructed and operative in accordance with still another embodiment of the present invention;

FIGS. 8A and 8B are respective simplified sectional illustrations of the construction of a real time selectable size reconstructive breast prosthesis constructed and operative in accordance with yet another embodiment of the present invention;

FIGS. 9A, 9B, 9C and 9D are respective simplified pictorial, cross sectional, longitudinal sectional and partially cut away side view illustrations of a reconstructive breast prosthesis constructed and operative in accordance with still a further embodiment of the present invention;

FIGS. 10A, 10B, 10C and 10D are respective simplified pictorial, cross sectional, longitudinal sectional and partially cut away side view illustrations of a reconstructive breast prosthesis constructed and operative in accordance with yet a further embodiment of the present invention;

FIG. 11 is a simplified illustration of a lumpectomy and subsequent treatment procedure in which a reconstructive breast prosthesis of the type shown in FIGS. 10A-10D, constructed and operative in accordance with a preferred embodiment of the invention, is inserted into a void resulting from the lumpectomy;

FIGS. 12A, 12B, 12C, 12D and 12E are simplified sectional and pictorial illustrations of various stages in the implantation and operation of a reconstructive breast prosthesis and associated pump constructed and operative in accordance with a preferred embodiment of the present invention;

FIGS. 13A, 13B, 13C, and 13D are respective simplified pictorial, cross sectional, longitudinal sectional and partially cut away side view illustrations of a reconstructive breast prosthesis constructed and operative in accordance with yet a further embodiment of the present invention;

FIGS. 14A, 14B, 14C, 14D, 14E, 14F and 14G are simplified sectional and pictorial illustrations of various stages in the implantation and therapeutic radiation procedure using operation of a multiple sealed volume reconstructive breast prosthesis constructed and operative in accordance with a preferred embodiment of the present invention; and FIGS. 15A, 15B, 15C and 15D are, respectively, pictorial top view, pictorial bottom view, first sectional and second sectional illustrations of an integrally formed internal skeletal element employed in an implantable tissue expander in accordance with a preferred embodiment of the present invention;

FIGS. 16A, 16B, 16C and 16D are, respectively, pictorial top view, pictorial bottom view, first sectional and second sectional illustrations of an integrally formed internal skeletal element employed in an implantable tissue expander in accordance with another preferred embodiment of the present invention;

FIGS. 17A, 17B, 17C and 17D are, respectively, pictorial top view, pictorial bottom view, first sectional and second sectional illustrations of an integrally formed internal skeletal element employed in an implantable tissue expander in accordance with yet another preferred embodiment of the present invention.

DETAILED DESCRIPTION OF PREFERRED EMBODIMENTS

Reference is now made to FIG. $I_9$ which is a simplified illustration of a lumpectomy procedure in which a body of tissue is excised from the breast and in which a reconstructive breast prosthesis constructed and operative in accordance with a preferred embodiment of the invention is inserted into a void resulting from the lumpectomy.

Figure 1:
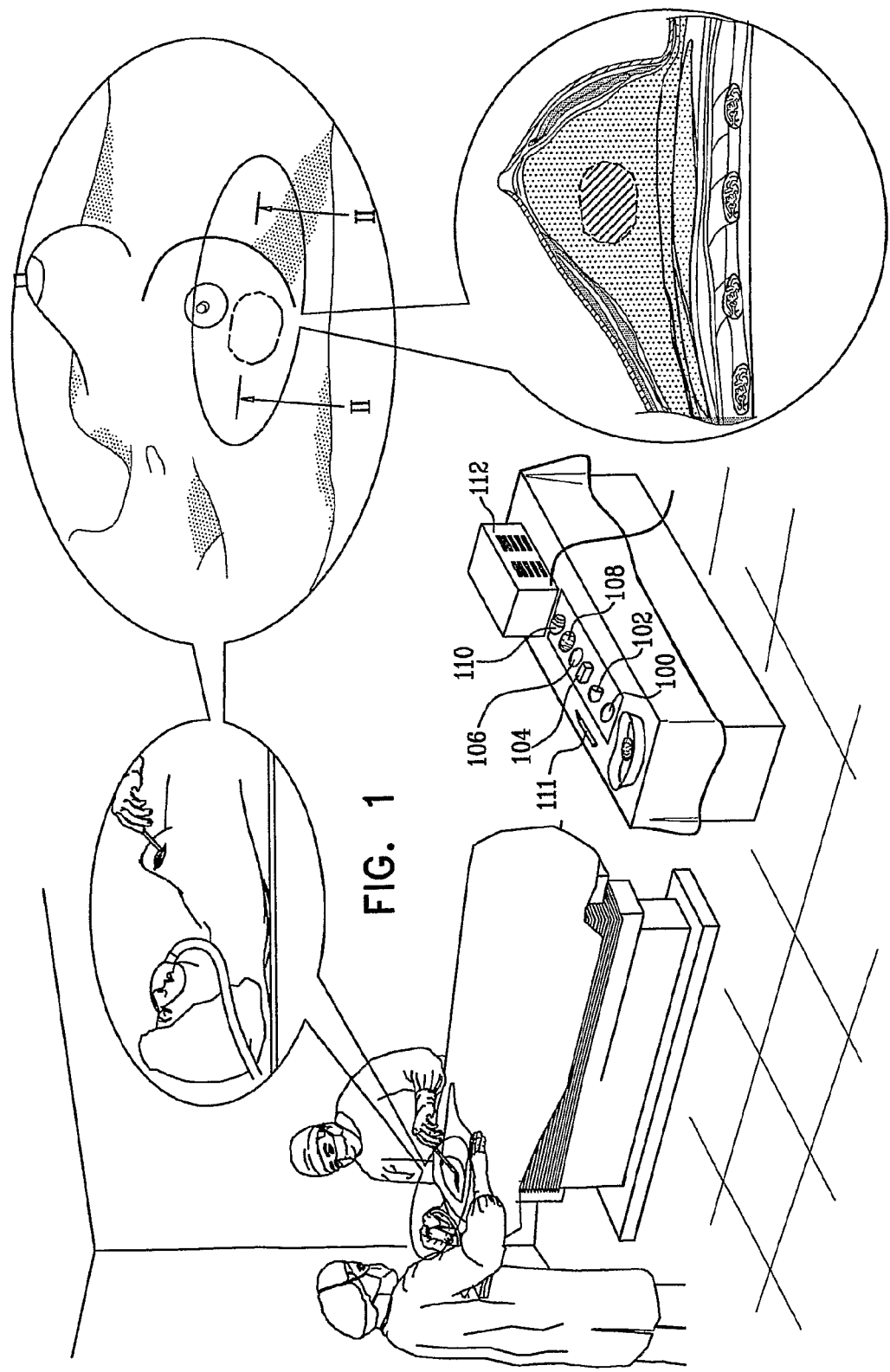
FIG. 1 is a simplified illustration of a lumpectomy procedure in which a reconstructive breast prosthesis constructed and operative in accordance with a preferred embodiment of the invention is inserted into a void resulting from the lumpectomy.

As seen in FIG. 1, preferably at the time of performing the lumpectomy, a plurality of differently shaped and sized reconstructive breast prostheses, indicated by reference numerals 100, 102, 104, 106, 108 and a reconstructive breast prosthesis assembly 110 are available for implantation. Assembly 110 is a selectable size implant assembly which may be selectably sized prior to or during the procedure by the use of a cutting implement 111 and a sealing device 112, such as heating device. It is appreciated that implantation need not necessarily take place immediately after the lumpectomy and may instead take place in a separate procedure.

Reference is now made to FIGS. 2A, 2B, 2C and 2D, which are simplified sectional and pictorial illustrations of various stages in the implantation of a resilient reconstructive breast prosthesis constructed and operative in accordance with a preferred embodiment of the present invention. It is appreciated that notwithstanding that a reconstructive breast prosthesis of the general shape corresponding to implant 100 is illustrated, the procedure illustrated in FIGS. 2A-2D is applicable to any suitable reconstructive breast prosthesis constructed and operative in accordance with the present invention, of which implants 100, 102, 104, 106 and 108 and assembly 110 are examples.

Figure 2A:
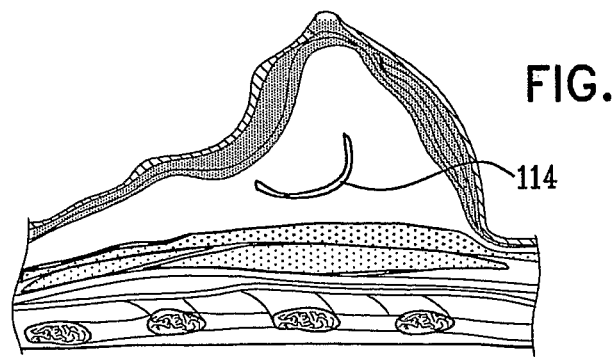
FIGS. 2A, 2B, 2C and 2D are simplified sectional and pictorial illustrations of various stages in the implantation of a reconstructive breast prosthesis constructed and operative in accordance with a preferred embodiment of the present invention.

FIG. 2A illustrates a breast following a lumpectomy and having a resulting void, designated by reference numeral 114. It is noted that the shape of the breast is somewhat deformed due to the presence of the void 114.

Figure 2B:
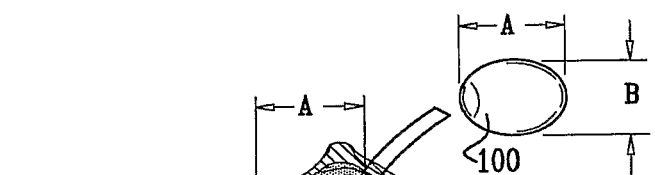
Figure 2C:
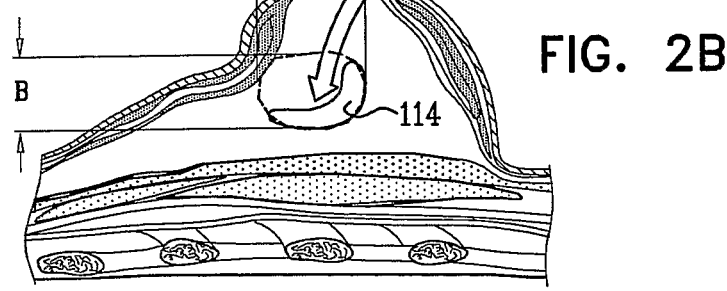
Figure 2D:
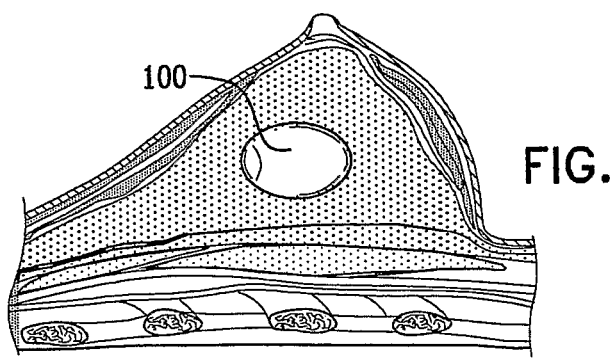
Figure 3A:
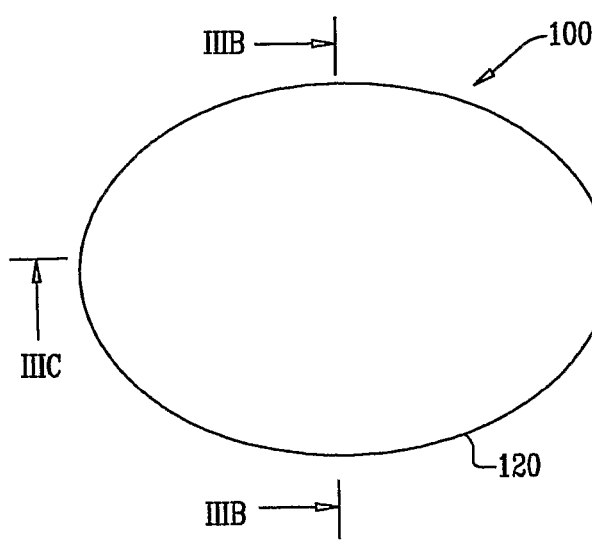
FIGS. 3A, 3B, 3C and 3D are respective simplified pictorial, cross sectional, longitudinal sectional and partially cut away side view illustrations of a reconstructive breast prosthesis constructed and operative in accordance with one embodiment of the present invention.
Figure 3B:
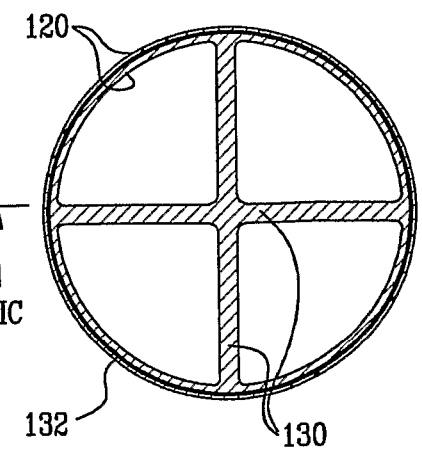
Figure 3C:
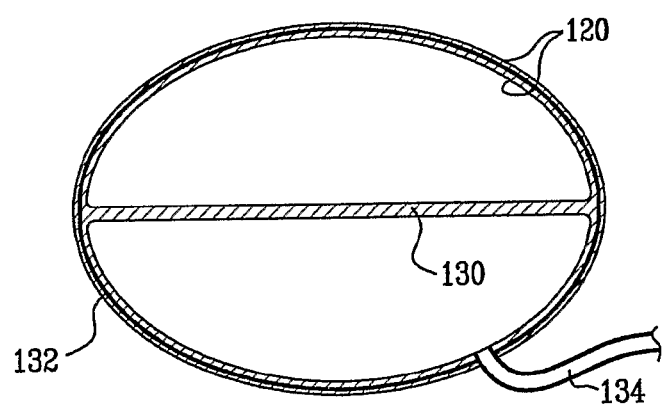
Figure 3D:
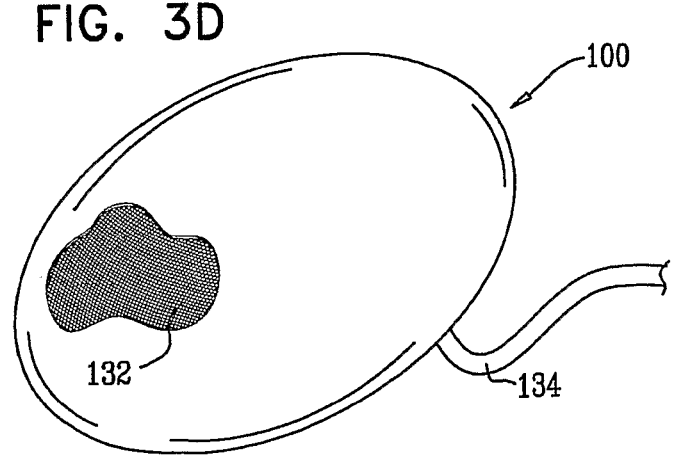
Figure 4A:
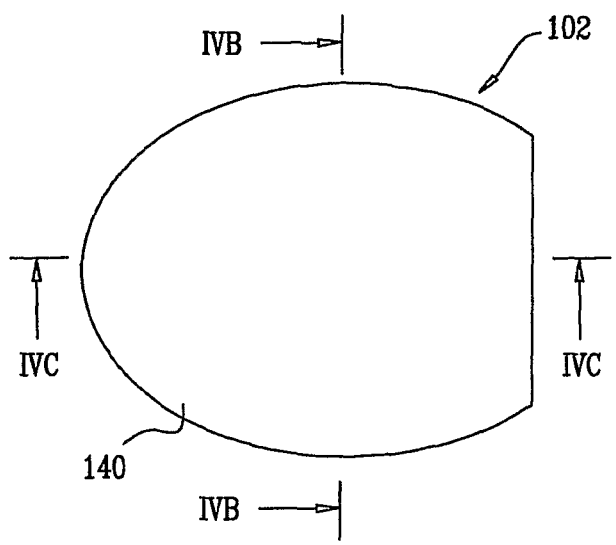
FIGS. 4A, 4B, 4C and 4D are respective simplified pictorial, cross sectional, longitudinal sectional and partially cut away side view illustrations of a reconstructive breast prosthesis constructed and operative in accordance with another embodiment of the present invention.
Figure 4B:
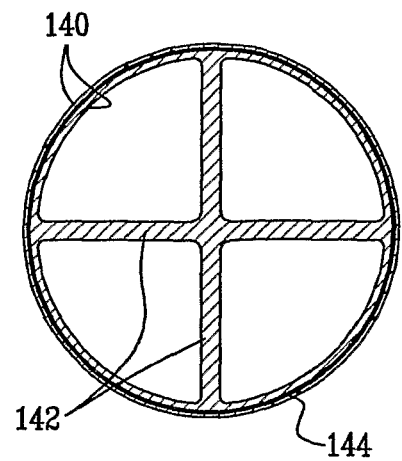
Figure 4C:
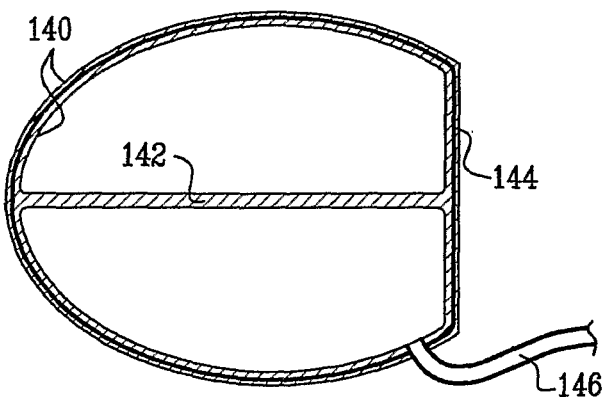
Figure 4D:
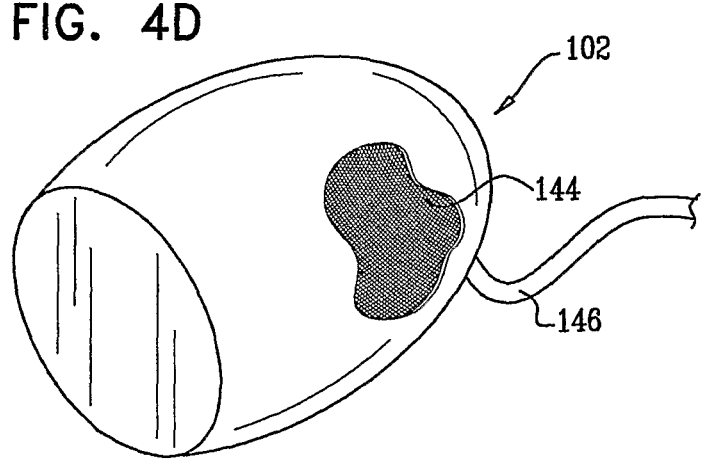
Figure 6A:
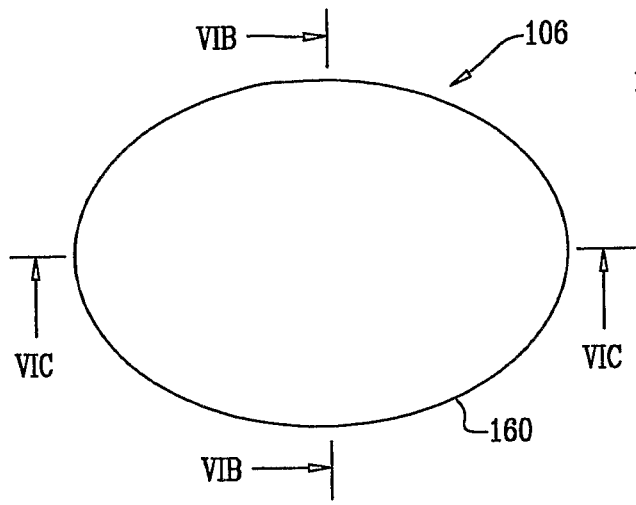
Figure 6B:
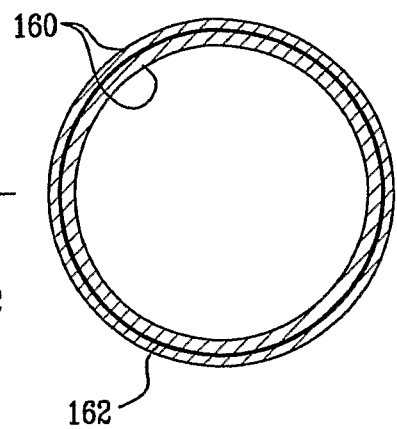
Figure 6C:
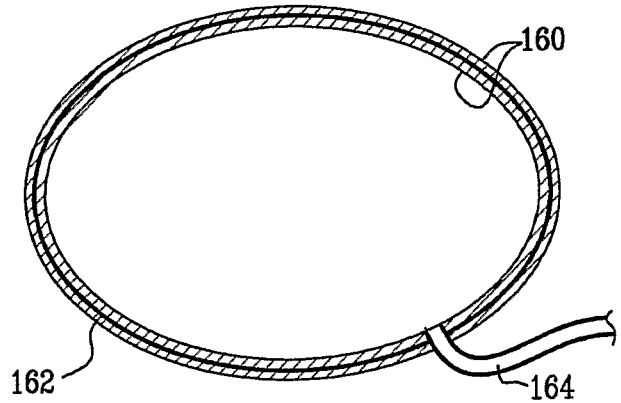
Figure 6D:
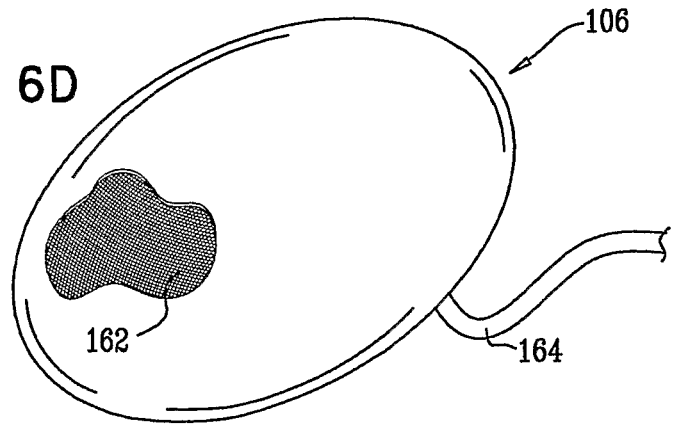

FIG. 2B illustrates insertion of a compressed, resilient reconstructive breast prosthesis 100 into void 114. FIG. 2C shows the resilient reconstructive breast prosthesis 100, following decompression thereof, which is surrounded by breast tissue and generally fills void 114 and eliminates the deformation of the breast seen in FIGS. 2A & 2B. FIG. 2D shows a sutured incision 116 alongside implant 100, which is surrounded by breast tissue. It is appreciated that the surrounding breast tissue supports the reconstructive breast prosthesis 100, which has a density less than that of the surrounding breast tissue.

Reference is now made to FIGS. 3A, 3B, 3C and 3D, which are respective simplified pictorial, cross sectional, longitudinal sectional and partially cut away side view illustrations of a reconstructive breast prosthesis 100 constructed and operative in accordance with one embodiment of the present invention. As seen in FIGS. 3A-3D, the prosthesis implant 100 preferably includes an implant body 120 which has a general egg shape and is supported by mutually perpendicular interior ribs 130, which are preferably integrally formed with implant body 120. The implant body 120 is preferably formed of a resilient biocompatible material, such as silicone, and preferably is molded together with a non-stretchable resilient mesh 132, typically formed of polyester or polyethylene, in order to prevent undesirable expansion thereof at low ambient pressures.

It is appreciated that in accordance with a preferred embodiment of the present invention both ribs 130 and mesh 132 serve as implant shape retaining structures, the ribs 130 acting to prevent collapse of the implant body 120 and the mesh 132 acting to prevent undesired expansion of the implant body 120 by defining a fixed surface area of the implant body. The material of which the implant body 120 is formed preferably has a shape memory which is also operative to resist collapse and undesired expansion, while preserving overall resilience.

The implant body 120 is preferably at least generally configured to correspond to the shape of a body of tissue excised from the breast and to have a sealed non-liquid filled interior. The prosthesis preferably has an overall density which is less than the density of the body of tissue excised from the breast. Preferably, the prosthesis has a specific gravity less than 0.9 g/cc and preferably less than about 0.5 g/cc.

An optional, selectably sealable and removable inflation/deflation tube 134 may be provided for selectable inflation or deflation of the implant body 120 prior to, during or following implantation thereof. Selectably sealable and removable inflation/deflation tube 134 is preferably sealed and may also be removed following implantation of reconstructive breast prosthesis 100.

Reference is now made to FIGS. 4A, 4B, 4C and 4D, which are respective simplified pictorial, cross sectional, longitudinal sectional and partially cut away side view illustrations of a reconstructive breast prosthesis 102 constructed and operative in accordance with, another embodiment of the present invention. As seen in FIGS. 4A-4D, the prosthesis implant 102 preferably includes an implant body 140 which has a generally truncated egg shape and is supported by mutually perpendicular interior ribs 142, which are preferably integrally formed therewith. The implant body 140 is preferably formed of a resilient biocompatible material, such as silicone, and preferably includes a non-stretchable resilient mesh 144, typically formed of polyester or polyethylene, to prevent undesirable expansion thereof at low ambient pressures.

It is appreciated that in accordance with a preferred embodiment of the present invention both ribs 142 and mesh 144 serve as implant shape retaining structures, the ribs 142 acting to prevent collapse of the implant body 140 and the mesh 144 acting to prevent undesired expansion of the implant body 140 by defining a fixed surface area of the implant body. The material of which the implant body 140 is formed preferably has a shape memory which is also operative to resist collapse and undesired expansion, while preserving overall resilience.

The implant body 140 is preferably at least generally configured to correspond to the shape of a body of tissue excised from the breast and to have a sealed non-liquid filled interior. The prosthesis preferably has an overall density which is less than the density of the body of tissue excised from the breast. Preferably, the prosthesis has a specific gravity less than 0.9 g/cc and preferably less than about 0.5 g/cc.

An optional, selectably sealable and removable inflation/deflation tube 146 may be provided for selectable inflation or deflation of the implant body 140 prior to, during or following implantation thereof. Selectably sealable and removable inflation/deflation tube 146 is preferably sealed and may also be removed following implantation of reconstructive breast prosthesis 102.

Reference is now made to FIGS. 5A, 5B, 5C and 5D, which are respective simplified pictorial, cross sectional, longitudinal sectional and partially cut away side view illustrations of a reconstructive breast prosthesis 104 constructed and operative in accordance with yet another embodiment of the present invention. As seen in FIGS. 5A-5D, the prosthesis implant 104 includes an implant body 150 having a general rectangular shape and being supported by mutually perpendicular interior ribs 152, which are preferably integrally formed therewith. The implant body 150 is preferably formed of a resilient biocompatible material, such as silicone, and preferably includes a non-stretchable resilient mesh 154, typically formed of polyester or polyethylene, to prevent undesirable expansion thereof at low ambient pressures.

It is appreciated that in accordance with a preferred embodiment of the present invention both ribs 152 and mesh 154 serve as implant shape retaining structures, the ribs 152 acting to prevent collapse of the implant body 150 and the mesh 154 acting to prevent undesired expansion of the implant body 150 by defining a fixed surface area of the implant body. The material of which the implant body 150 is formed preferably has a shape memory which is also operative to resist collapse and undesired expansion, while preserving overall resilience.

The implant body 150 is preferably at least generally configured to correspond to the shape of a body of tissue excised from the breast and to have a sealed non-liquid filled interior. The prosthesis preferably has an overall density which is less than the density of the body of tissue excised from the breast. Preferably, the prosthesis has a specific gravity less than 0.9 g/cc and preferably less than about 0.5 g/cc.

An optional, selectably sealable and removable inflation/deflation tube 156 may be provided for selectable inflation or deflation of the implant body 150 prior to, during or following implantation thereof. Selectably sealable and removable inflation/deflation tube 156 is preferably sealed and may also be removed following implantation of reconstructive breast prosthesis 104.

Reference is now made to FIGS. 6A, 6B, 6C and 6D, which are respective simplified pictorial, cross sectional, longitudinal sectional and partially cut away side view illustrations of a reconstructive breast prosthesis 106 constructed and operative in accordance with still another embodiment of the present invention. As seen in FIGS. 6 A-6D, the implant 106 includes an implant body 160 having a general egg shape which is unsupported by ribs. The implant body 160 is preferably formed of a resilient biocompatible material, such as silicone and preferably includes a non-stretchable resilient mesh 162, typically formed of polyester or polyethylene, to prevent undesirable expansion thereof at low ambient pressures.

It is appreciated that in accordance with a preferred embodiment of the present invention, mesh 162 serves as an implant shape retaining structure, the mesh 162 acting to prevent undesired expansion of the implant body 160 by defining a fixed surface area of the implant body 160. The material of which the implant body 160 is formed preferably has a shape memory, which is also operative to resist collapse and undesired expansion, while preserving overall resilience.

The implant body 160 is preferably at least generally configured to correspond to the shape of a body of tissue excised from the breast and to have a sealed non-liquid filled interior. The prosthesis preferably has an overall density which is less than the density of the body of tissue excised from the breast. Preferably, the prosthesis has a specific gravity less than 0.9 g/cc and preferably less than about 0.5 g/cc.

An optional, selectably sealable and removable inflation/deflation tube 164 may be provided for selectable inflation or deflation of the implant body 160 prior to, during or following implantation thereof. Selectably sealable and removable inflation/deflation tube 164 is preferably sealed and may also be removed following implantation of reconstructive breast prosthesis 106.

Figures 7A, 7B:
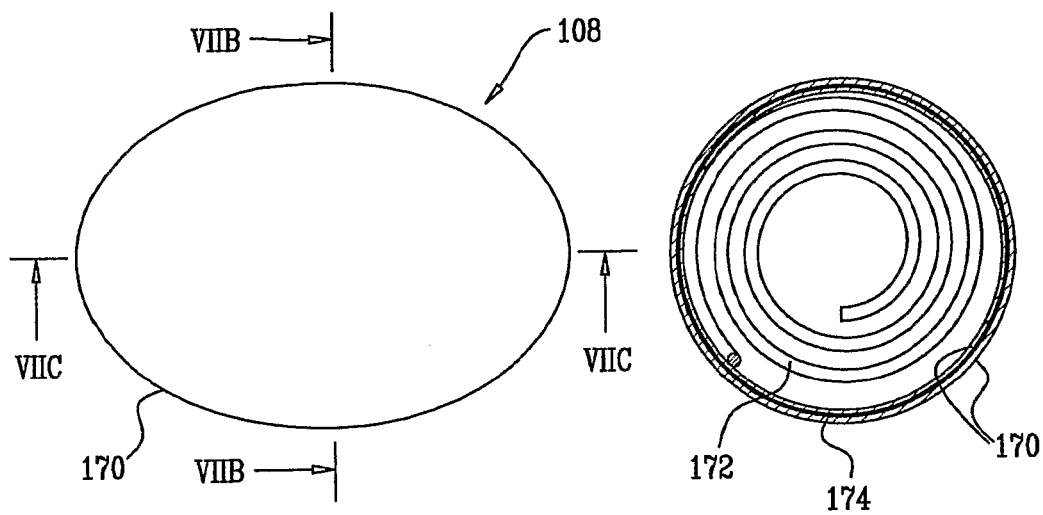
Figure 7C:
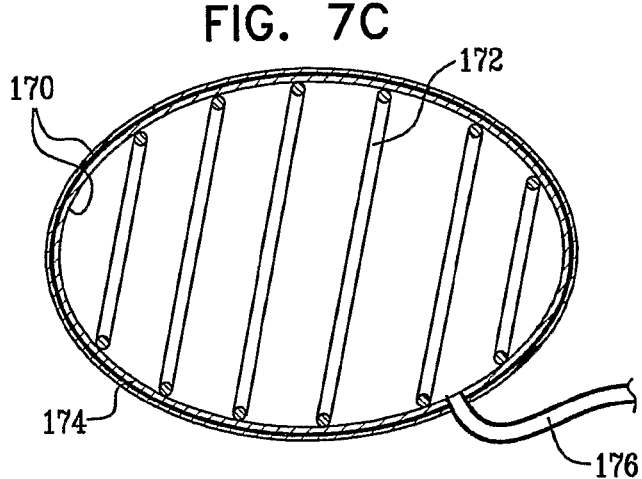
Figure 7D:
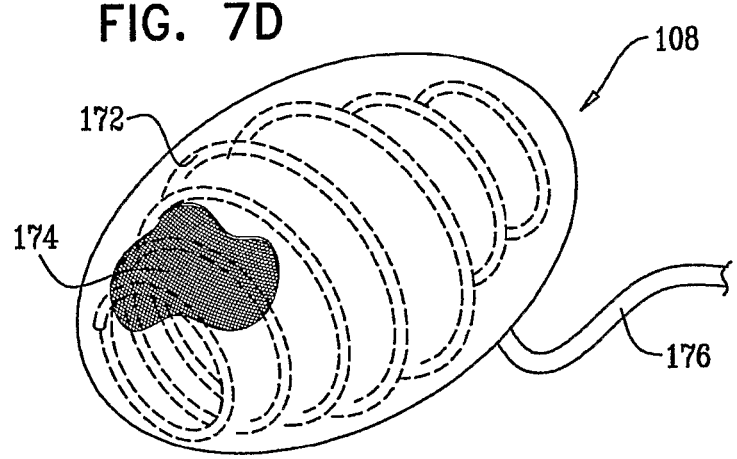

Reference is now made to FIGS. 7 A, 7B, 7C and TD, which are respective simplified pictorial, cross sectional, longitudinal sectional and partially cut away side view illustrations of a reconstructive breast prosthesis 108 constructed and operative in accordance with yet another embodiment of the present invention. As seen in FIGS. 7A-7D, the prosthesis implant 108 includes an implant body 170 which has a general egg shape and is supported by an interior coil spring 172, which is preferably integrally formed therewith. The implant body 170 and the interior coil spring 172 are preferably formed of a resilient biocompatible material, such as silicone, and the implant body 170 preferably includes a non-stretchable resilient mesh 174, typically formed of polyester or polyethylene, to prevent undesirable expansion thereof at low ambient pressures.

It is appreciated that in accordance with a preferred embodiment of the present invention both spring 172 and mesh 174 serve as implant shape retaining structures, the spring 172 acting to prevent collapse of the implant body 170 and the mesh 174 acting to prevent undesired expansion of the implant body 170 by defining a fixed surface area of the implant body. The material of which the implant body 170 is formed preferably has a shape memory which is also operative to resist collapse and undesired expansion, while preserving overall resilience.

The implant body 170 is preferably at least generally configured to correspond to the shape of a body of tissue excised from the breast and to have a sealed non-liquid filled interior. The prosthesis preferably has an overall density which is less than the density of the body of tissue excised from the breast. Preferably, the prosthesis has a specific gravity less than 0.9 g/cc and preferably less than about 0.5 g/cc.

An optional, selectably sealable and removable inflation/deflation tube 176 may be provided for selectable inflation or deflation of the implant body 170 prior to, during or following implantation thereof. Selectably sealable and removable inflation/deflation tube 176 is preferably sealed and may also be removed following implantation of reconstructive breast prosthesis 108.

Reference is now made to FIGS. 8A and 8B, which are respective simplified sectional illustrations of the construction of a real time selectable size reconstructive breast prosthesis assembly 110 constructed and operative in accordance with yet another embodiment of the present invention. As seen in FIGS. 8A-8B, the reconstructive breast prosthesis assembly comprises a main body portion 190 which may be cut to a desired longitudinal length by cutting implement 111 (FIG. 1) and sealed by a cap portion 192, the sealing preferably being effected by the use of a silicone glue which is cured by heating, preferably applied by sealing device 112, such as an oven. It is appreciated that sizing of the resulting implant body of assembly 110 may take place during the implantation procedure or, alternatively, prior thereto. It is appreciated that other types of real-time sizing of the implants are also encompassed within the scope of the present invention.

As seen in FIGS. 8A-8B, the prosthesis implant produced by selectable sizing of assembly 110, here designated by reference numeral 194, has a generally truncated egg shape and is supported by one or more ribs 196. The entire prosthesis assembly 110 is preferably formed of a resilient biocompatible material, such as silicone, and preferably includes a non-stretchable resilient mesh 198 to prevent undesirable expansion thereof at low ambient pressures.

An optional, selectably sealable and removable inflation/deflation tube 200 may be provided for selectable inflation or deflation of the implant 194 prior to, during or following implantation thereof. Selectably sealable and removable inflation/deflation tube 200 is preferably sealed and may also be removed following implantation of implant 194.

Reference is now made to FIGS. 9A, 9B, 9C and 9D, which are respective simplified pictorial, cross sectional, longitudinal sectional and partially cut away side view illustrations of a reconstructive breast prosthesis 208 constructed and operative in accordance with yet a further embodiment of the present invention. As seen in FIGS. 9A-9D, the prosthesis implant 208 includes an implant body 270 which has a general egg shape and is supported by an interior coil spring 272, which is preferably integrally formed therewith. The implant body 270 and the interior coil spring 272 are preferably formed of a resilient biocompatible material, such as silicone, and the implant body 270 preferably includes a non-stretchable resilient mesh 274, typically formed of polyester or polyethylene, to prevent undesirable expansion thereof at low ambient pressures.

It is appreciated that in accordance with a preferred embodiment of the present invention both spring 272 and mesh 274 serve as implant shape retaining structures, the spring 272 acting to prevent collapse of the implant body 270 and the mesh 274 acting to prevent undesired expansion of the implant body 270 by defining a fixed surface area of the implant body. The material of which the implant body 270 is formed preferably has a shape memory which is also operative to resist collapse and undesired expansion, while preserving overall resilience.

The implant body 270 is preferably at least generally configured to correspond to the shape of a body of tissue excised from the breast and to have a sealed non-liquid filled interior. The prosthesis preferably has an overall density which is less than the density of the body of tissue excised from the breast.

Preferably, the prosthesis has a specific gravity less than 0.9 g/cc and preferably less than about 0.5 g/cc.

In accordance with a preferred embodiment of the present invention, first and second mutually opposed injection ports 280 and 282 are integrated into an outer wall 284 of implant body 270. Preferably the injection ports 280 and 282 are arranged so as to be readily accessible for hypodermic injection and drainage and once implanted are located with respect to the patient such that port 282 lies below port 280. The injection ports may be used for injection of therapeutic liquids to the interior of implant body 270 and removal of such liquids or air therefrom, as appropriate. Injection ports 280 and 282 are examples of self-sealing ports which may be advantageously employed in all suitable embodiments described herein. In the embodiments of FIGS. 3A-7D, FIGS. 9A-10D and 13A-BD self-sealing ports may be provided to couple the interior of an implant body of a prosthesis to one or. more tubes.

The therapeutic liquid can be a combination of any suitable solvent and any drug, chemical compound, radioactive material, naturally occurring hormone, artificially made hormone, growth factor, antibodies to block receptors on cell membranes, antibodies to block receptors within a target cell, or any naturally occurring or artificially made molecule intended to alter physiological or pathological processes locally or generally in the body to treat or to prevent a disease. For example, introduction and subsequent removal of radioactive materials from the implant body 270 can provide precisely timed and location controllable radiation therapy. Drugs or other liquids and/or their solvents may be selected so as to be permeable through the wall 284 so as to provide therapeutic treatment of the surrounding tissue.

The therapeutic liquid may be injected into the implant inner volume through injection port 280 while port 282 is used for venting air out of the implant. Lower placed injection port 282 is preferably used for drawing out and irrigating the therapeutic liquid from the interior of the implant 208 following treatment. When irrigating the interior of implant body 270, an irrigating solution may be injected through the upper injection port 280 and the irrigating solution may be drained through the lower port 282.

An optional, selectably sealable and removable inflation/deflation tube 286 may be provided for selectable inflation or deflation of the implant body 270 prior to, during or following implantation thereof. Selectably sealable and removable inflation/deflation tube 286 is preferably sealed and may also be removed following implantation of reconstructive breast prosthesis 208.

Reference is now made to FIGS. 10A, 10B, 10C and 10D, which are respective simplified pictorial, cross sectional, longitudinal sectional and partially cut away side view illustrations of a reconstructive breast prosthesis 308 constructed and operative in accordance with yet a further embodiment of the present invention. As seen in FIGS. 10A-10D, the implant 308 includes an implant body 370 which has a general egg shape and is supported by an interior coil spring 372, which is preferably integrally formed therewith. The implant body 370 and the interior coil spring 372 are preferably formed of a resilient biocompatible material, such as silicone, and the implant body 370 preferably includes a non-stretchable resilient mesh 374, typically formed of polyester or polyethylene, to prevent undesirable expansion thereof at low ambient pressures.

It is appreciated that in accordance with a preferred embodiment of the present invention both spring 372 and mesh 374 serve as implant shape retaining structures, the spring 372 acting to prevent collapse of the implant body 370 and the mesh 374 acting to prevent undesired expansion of the implant body 370 by defining a fixed surface area of the implant body. The material of which the implant body 370 is formed preferably has a shape memory which is also operative to resist collapse and undesired expansion, while preserving overall resilience.

The implant body 370 is preferably at least generally configured to correspond to the shape of a body of tissue excised from the breast and to have a sealed non-liquid filled interior.

Optionally, in accordance with a preferred embodiment of the present invention, first and second mutually opposed injection ports 380 and 382 may be integrated into an outer wall 384 of implant body 370. Preferably, the injection ports 380 and 382 are arranged so as to be readily accessible for hypodermic injection and drainage and once implanted are located with respect to the patient such that port 382 lies below port 380. The injection ports may be used for injection of therapeutic liquids to the interior of implant body 370 and removal of such liquids or air therefrom, as appropriate.

The therapeutic liquid can be a combination of any suitable solvent and any drug, chemical compound, radioactive material, naturally occurring hormone, artificially made hormone, growth factor, antibodies to block receptors on cell membranes, antibodies to block receptors within a target cell, or any naturally occurring or artificially made molecule intended to alter physiological or pathological processes locally or generally in the body to treat or to prevent a disease. For example, introduction and subsequent removal of radioactive materials from the implant body 370 can provide precisely timed and location controllable radiation therapy. Drugs or other liquids and/or their solvents may be selected so as to be permeable through the wall 384 so as to provide therapeutic treatment of the surrounding tissue.

The therapeutic liquid may be injected into the implant inner volume through injection port 380 while port 382 is used for venting air out of the implant. Lower placed injection port 382 is preferably used for drawing out and irrigating the therapeutic liquid from the interior of the implant 308 following treatment. When irrigating the interior of implant body 370, an irrigating solution may be injected through the upper injection port 380 and drained through the lower port 382.

In accordance with a preferred embodiment of the present invention, an optional, preferably selectably sealable and removable inflation/deflation tube 386 and associated implantable pump 388 may be provided for selectable dispensing of therapeutic liquids stored in the interior of implant body 370, which functions as a reservoir for such liquid. The therapeutic liquid may be dispensed to tissue surrounding an outlet of pump 388, in the direction shown by arrows 390.

The therapeutic liquid may be present in the interior of the implant body 370 at the time of implantation or may subsequently be supplied thereto, as via injection port 380. The pump 388 may be a conventional implantable pump and may dispense the therapeutic liquid in response to real time or pre-programmed commands. Tube 386 and pump 388 may be removed, as appropriate, following implantation of reconstructive breast prosthesis 308. Alternatively, pump 388 may be located interiorly of the implant body 370.

The prosthesis, excluding pump 388, preferably has an overall density which is less than the density of the body of tissue excised from the breast. Preferably, the prosthesis, excluding pump 388, has a specific gravity less than 0.9 g/cc and preferably less than about 0.5 g/cc.

Reference is now made to FIG. 11, which is a simplified illustration of a lumpectomy procedure in which a reconstructive breast prosthesis 400 of the type illustrated in FIGS. 10A-10D, constructed and operative in accordance with a preferred embodiment of the invention, is inserted into a void resulting from the lumpectomy in which a body of tissue is excised from the breast. As seen in FIG. 11, preferably at the time of performing the lumpectomy, a plurality of differently shaped and sized reconstructive breast prostheses, indicated by reference numerals 400, 402, 404, 406, 408 and a reconstructive breast prosthesis assembly 410 are available for implantation. Assembly 410 is a selectable size implant assembly which may be selectably sized prior to or during the procedure by the use of a cutting implement 411 and a sealing device 412, such as heating device. It is appreciated that implantation need not necessarily take place immediately after the lumpectomy and may instead take place in a separate procedure. Additionally, as seen in FIG. 11, a pump assembly 414, including an implantable pump 416 and associated tubes 418 is also available for implantation.

Preferably, the prosthesis, excluding pump assembly 414, has a specific gravity less than 0.9 g/cc and preferably less than about 0.5 g/cc.

Reference is now made to FIGS. 12A, 12B, 12C, 12D and 12E, which are simplified sectional and pictorial illustrations of various stages in the implantation of a resilient reconstructive breast prosthesis constructed and operative in accordance with a preferred embodiment of the present invention. It is appreciated that notwithstanding that a reconstructive breast prosthesis of the general shape corresponding to implant 400 is illustrated, the procedure illustrated in FIGS. 12A-12E is applicable to any suitable reconstructive breast prosthesis constructed and operative in accordance with the present invention, of which implants 400, 402, 404, 406 and 408 and assembly 410 are examples.

Figure 12A:
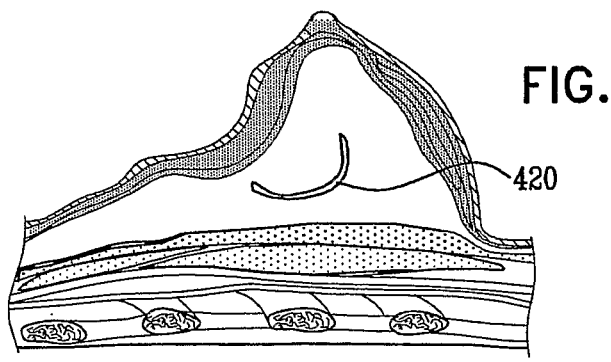

FIG. 12A illustrates a breast following a lumpectomy and having a resulting void, designated by reference numeral 420. It is noted that the shape of the breast is somewhat deformed due to the presence of the void 420.

Figure 12B:
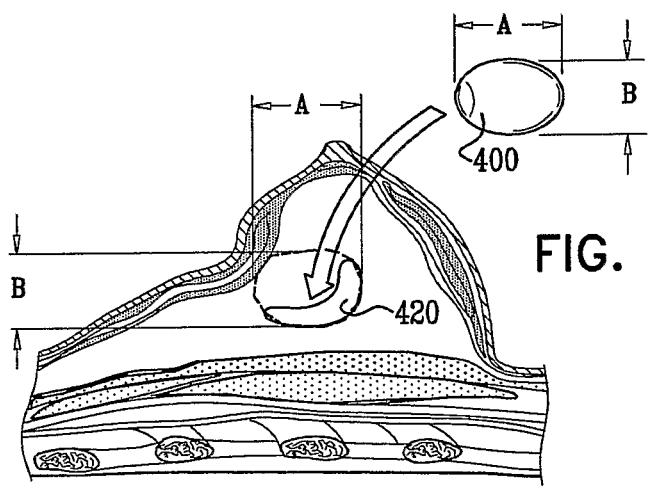
Figure 12C:
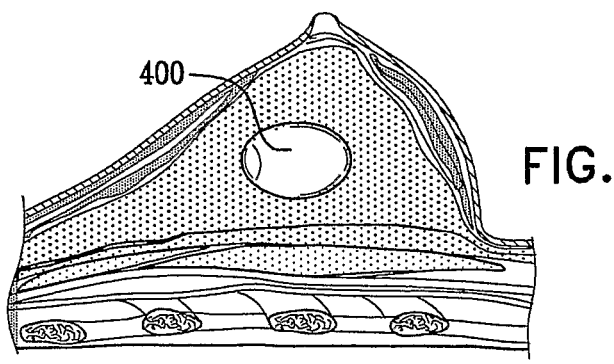
Figure 12D:
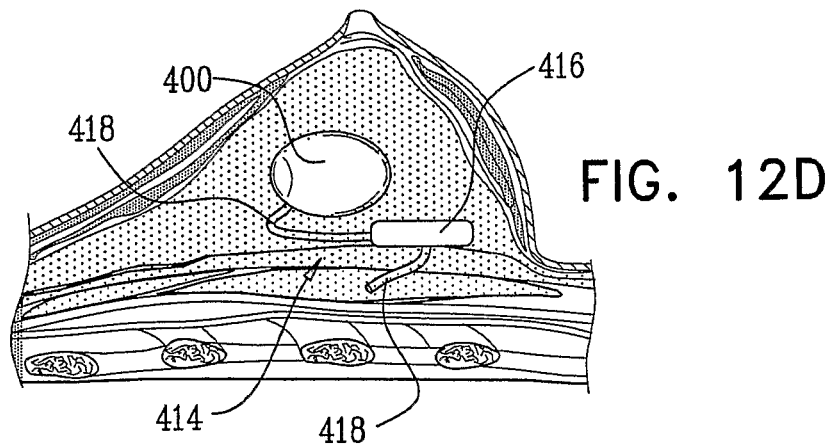

FIG. 12B illustrates insertion of a compressed, resilient reconstructive breast prosthesis 400 into void 420. FIG. 12C shows the resilient reconstructive breast prosthesis 400, following decompression thereof, which is surrounded by breast tissue and generally fills void 420 and eliminates the deformation of the breast seen in FIGS. 12A & 12B. FIG. 12D shows the connection of pump assembly 414, including implantable pump 416 and associated tubes 418, to implant 400. As described hereinabove, it is appreciated that pump assembly 414 may be removed, as appropriate, following implantation and prior to final suturing, or may be retained in the breast with or interiorly of prosthesis 400.

Figure 12E:
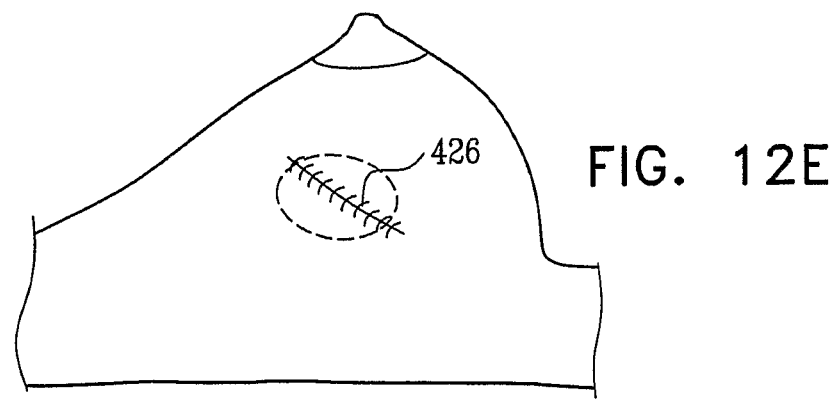

FIG. 12E shows a sutured incision 426 alongside prosthesis implant 400, which is surrounded by breast tissue. It is appreciated that the surrounding breast tissue supports the reconstructive breast prosthesis 400, which has a density less than that of the surrounding breast tissue.

Reference is now made to FIGS. 13A, 13B, 13C and 13D, which are respective simplified pictorial, cross sectional, longitudinal sectional and partially cut away side view illustrations of a multiple sealed volume reconstructive breast prosthesis 508 constructed and operative in accordance with yet a further embodiment of the present invention. As seen in FIGS. 13A-13D, the implant 508 includes an implant body 570 which has a general egg shape and is supported by an interior coil spring 572, which is preferably integrally formed therewith. The implant body 570 and the interior coil spring 572 are preferably formed of a resilient biocompatible material, such as silicone, and the implant body 570 preferably includes a non-stretchable resilient mesh 574, typically formed of polyester or polyethylene, to prevent undesirable expansion thereof at low ambient pressures.

It is appreciated that in accordance with a preferred embodiment of the present invention both spring 572 and mesh 574 serve as implant shape retaining structures, the spring 572 acting to prevent collapse of the implant body 570 and the mesh 574 acting to prevent undesired expansion of the implant body 570 by defining a fixed surface area of the implant body. The material of which the implant body 570 is formed preferably has a shape memory which is also operative to resist collapse and undesired expansion, while preserving overall resilience.

The implant body 570 is preferably at least generally configured to correspond to the shape of a body of tissue excised from the breast and to have a sealed non-liquid filled interior. The prosthesis preferably has an overall density which is less than the density of the body of tissue excised from the breast. Preferably, the prosthesis has a specific gravity less than 0.9 g/cc and preferably less than about 0.5 g/cc.

In accordance with a preferred embodiment of the present invention, an optional, preferably selectably sealable and removable inflation/deflation tube 586 may be provided for selectable dispensing of therapeutic liquids stored in the interior of implant body 570, which functions as a reservoir for such liquid. The therapeutic liquid may be pre-loaded into the implant body prior to implantation or more preferably supplied thereto following implantation. Tube 586 may be removed, as appropriate, following implantation of reconstructive breast prosthesis 508.

In accordance with a preferred embodiment of the present invention, additional sealed compartments are defined by the prosthesis 508, preferably within a double walled structure which defines the implant body 570. As seen particularly in FIGS. 13B-13D, the double walled structure includes an outer wall 588 and an inner wall 589 which are separated by a multiplicity of spacers 590. Preferably mesh 574 is associated with both walls 588 and 589. In the illustrated embodiment, the volume between walls 588 and 589 is divided into two mutually sealed volumes 591 and 592. It is appreciated that the volume between walls 588 and 589 may alternatively define any desired number of sealed volumes, which are also sealed from the interior of implant body 570.

In the illustrated embodiment of FIGS. 13A-13D, each of mutually sealed volumes 591 and 592 is supplied with respective ingress and egress tubes, respectively designated by reference numerals 593 and 594. Tubes 593 and 594 of each of volumes 591 and 592 preferably are associated with self-sealing ports (not shown).

Reference is now made to FIGS. 14A, 14B, 14C, 14D, 14E, 14F and 14G, which are simplified sectional and pictorial illustrations of various stages in the implantation and therapeutic radiation procedure using operation of a multiple sealed volume reconstructive breast prosthesis of the type described hereinabove with reference to FIGS. 13A-13D, constructed and operative in accordance with a preferred embodiment of the present invention. In this embodiment twelve mutually sealed volumes are defined between walls 588 and 589 of prosthesis 508. These mutually sealed volumes are designated in FIGS. 14A-14G by designations I, II, III, IV, V, VI, VII, VIII, IX, X, XI and XII. The ingress tubes communicating with each volume are each designated by reference numeral 593 and the corresponding egress tubes are each designated by reference numeral 594. The bundle of all of the tubes 593 and 594 is designated by reference numeral 595.

It is noted that although FIGS. 14A-14G illustrate a lumpectomy procedure, the present invention as described throughout FIGS. 1-14G is applicable to more extensive procedures wherein substantial portions or even all of the subcutaneous breast tissue is removed.

Figure 14A:
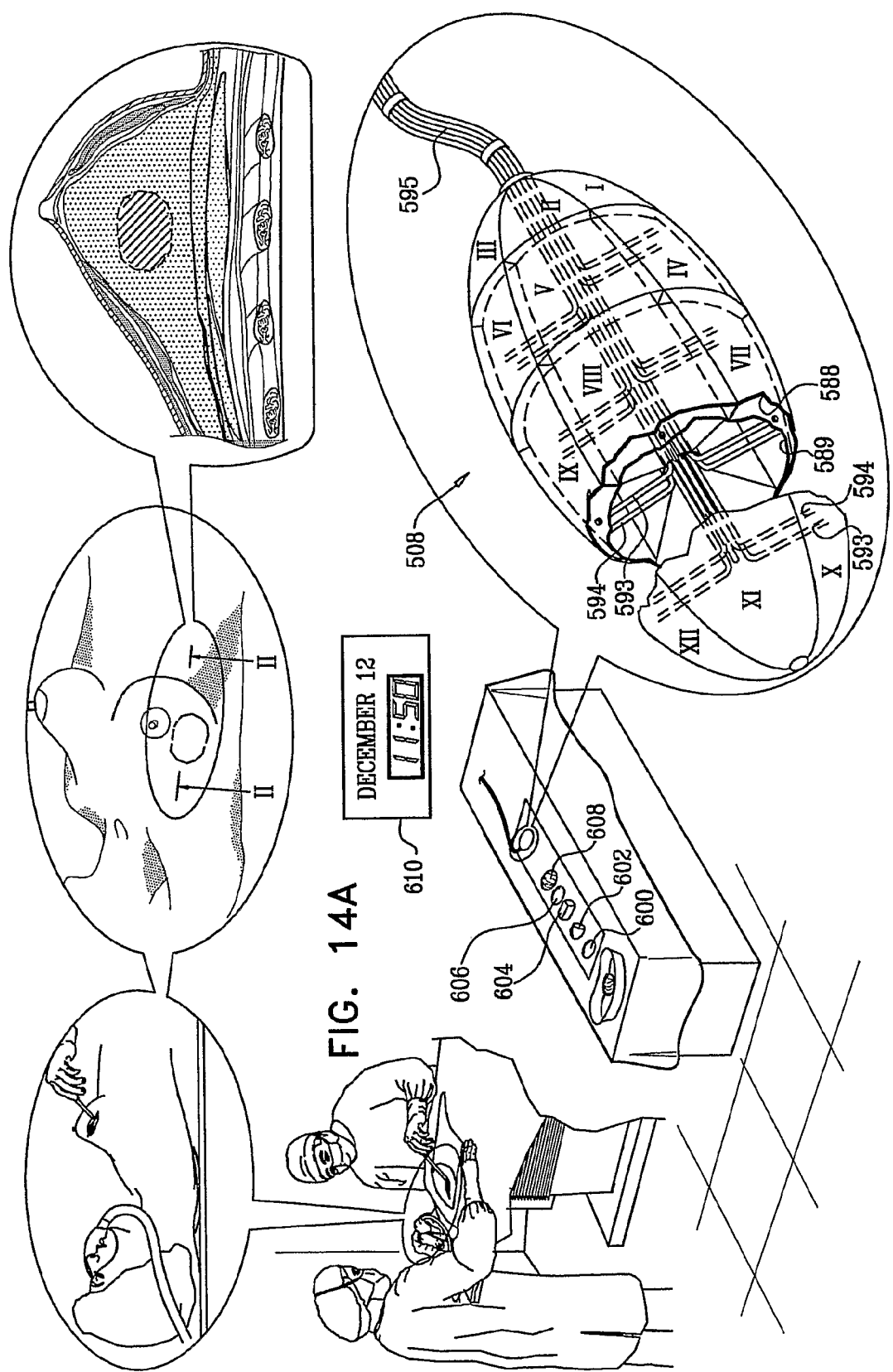

As seen in FIG. 14A, preferably at the time of performing the lumpectomy, a plurality of differently shaped and sized reconstructive breast prostheses, indicated by reference numerals 600, 602, 604, 606, 608 are available for implantation.

Figures 14B, 14C:
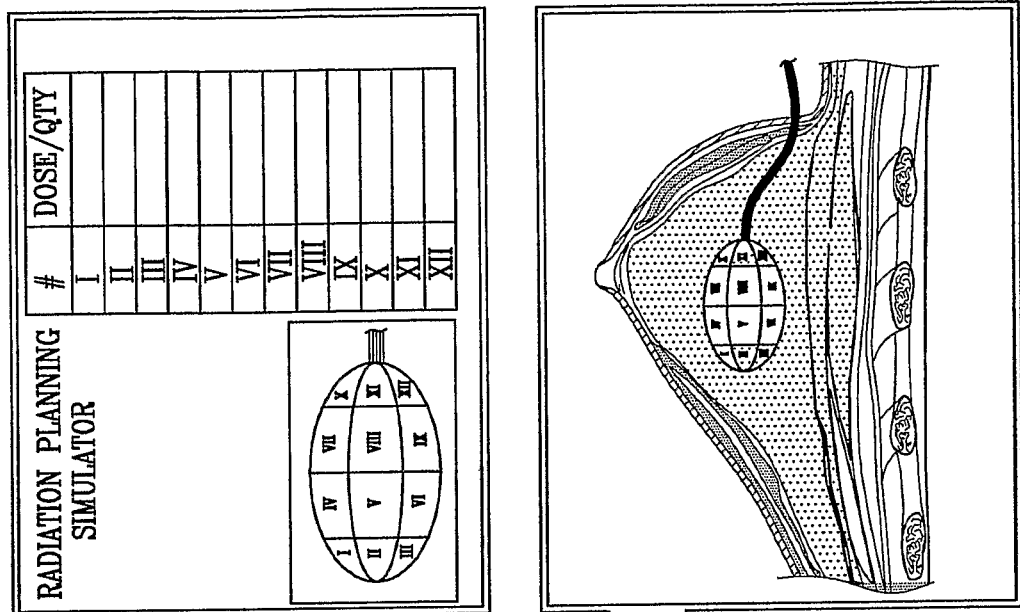

In accordance with a preferred embodiment of the present invention, as seen in FIG. 14B, the multiple sealed volume reconstructive breast prosthesis 508 is implanted in the same surgical procedure subsequent to the lumpectomy. This is indicated symbolically by a date and time clock 610 appearing in FIGS. 14A and 14B. It is appreciated that alternatively implantation need not necessarily take place immediately after the lumpectomy and may instead take place in a separate procedure. The implantation procedure may be similar to that illustrated in FIGS. 2A-2D and described hereinabove.

At a suitable time following the foregoing procedures, as seen in FIG. 14C, a radiation planning and simulation procedure is carried out off-line by a radiation professional using a computer system having commercially available radiation planning and simulation functionality such as embodied in Acuity™, Eclipse™, BrachiVision™ and Vitesse™ treatment planning software commercially available from Varian Medical Systems USA. The radiation dose to be provided by radioactive material in each of the mutually sealed volumes I-XII is calculated.

Figure 14D:
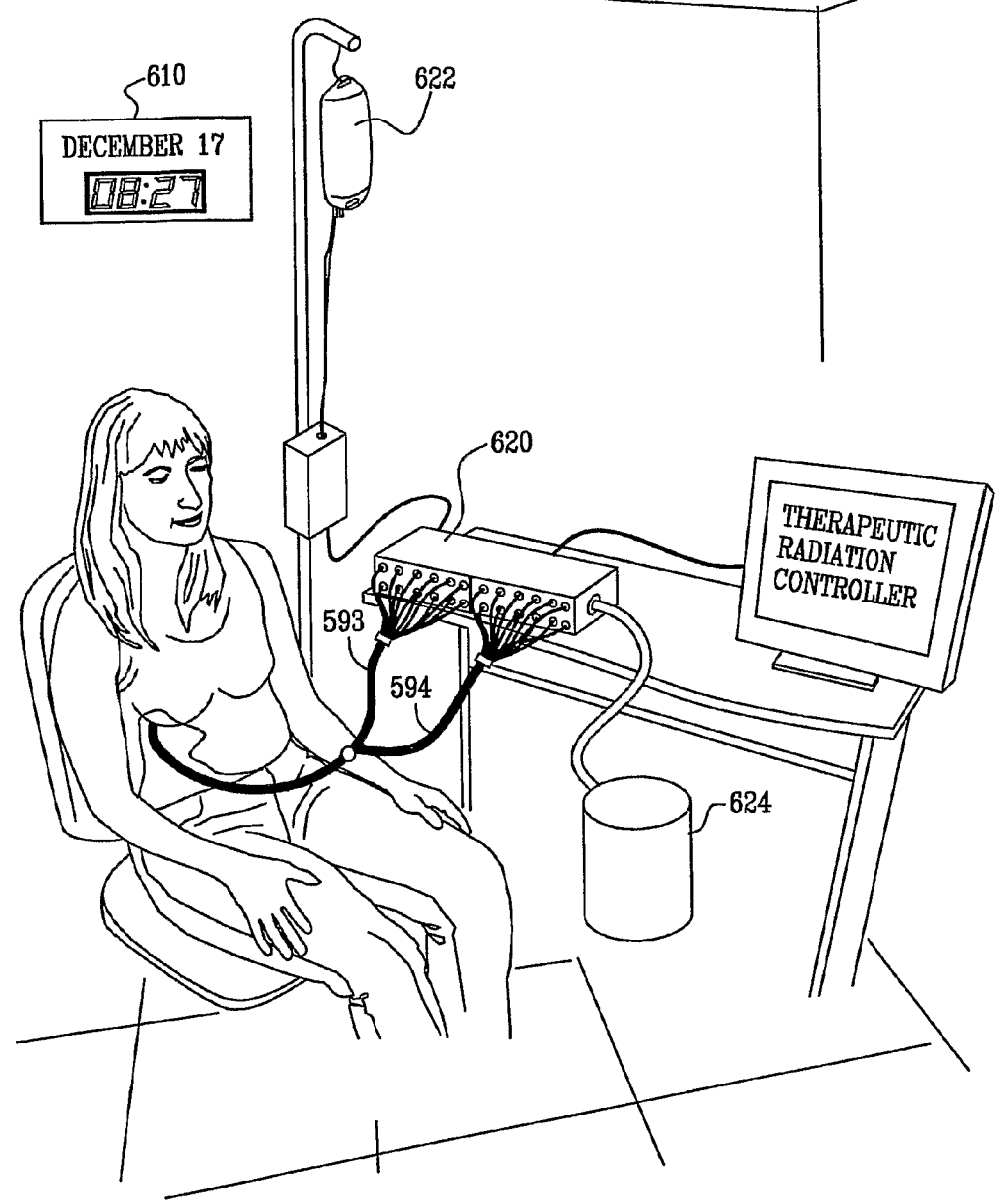

FIG. 14D illustrates radiation treatment of the patient, typically a few days after the lumpectomy. A computer controlled radioactive material dispenser 620, such as a Varisource™ iX afterloader, commercially available from Varian Medical Systems USA, supplies a suitable amount of radioactive material from a reservoir 622 to each of sealed volumes I-XII via ingress tubes 593.

Figure 14E:
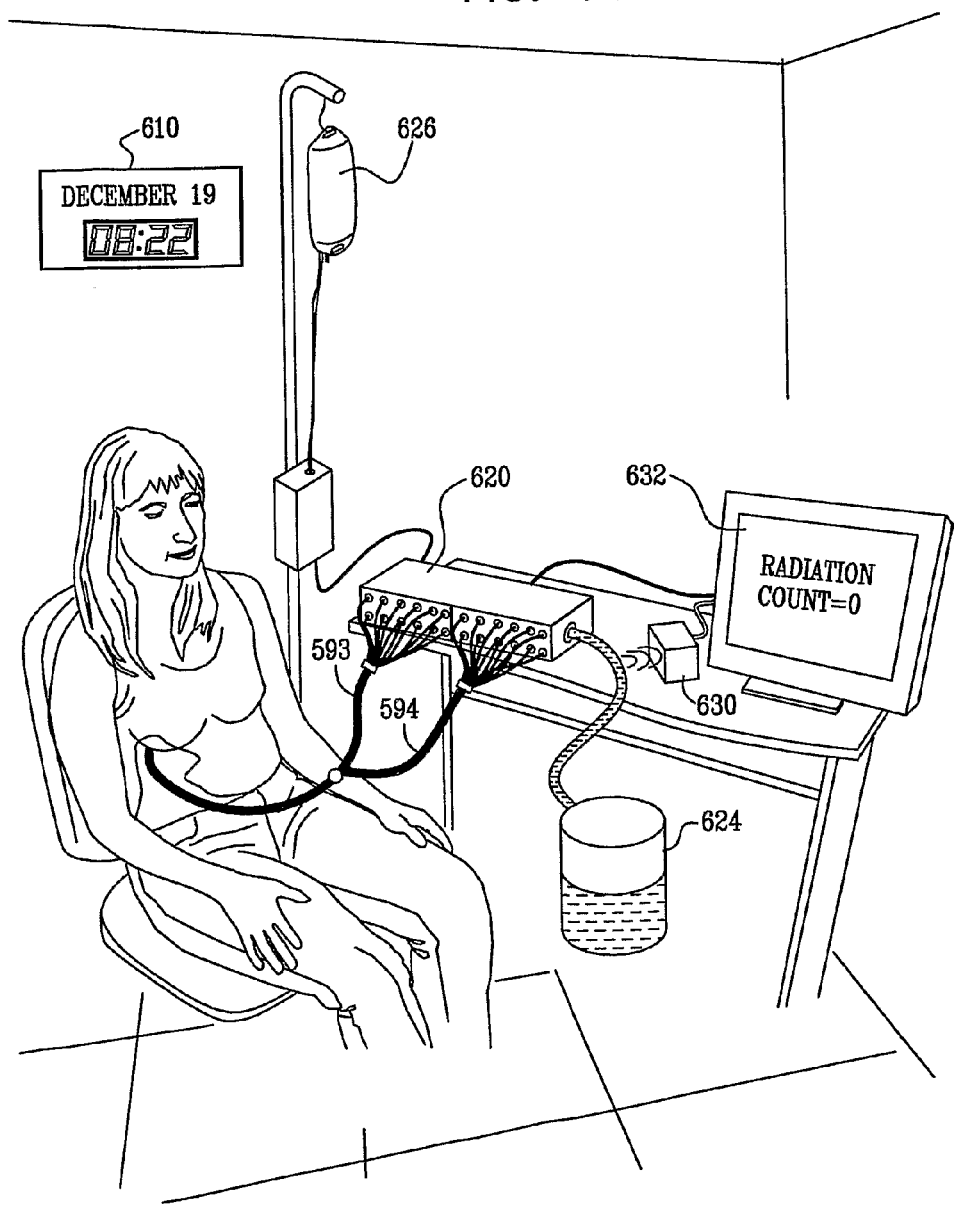

As seen in FIG. 14E, after a suitable amount of time, the radioactive material is flushed from sealed volumes I-XII via egress tubes 594 into a disposal vessel 624 preferably by use of an irrigation liquid supplied from a reservoir 626 via ingress tubes 593. The absence of residual radioactive material in the prosthesis 508 is preferably confirmed by the use of a suitable radiation detector 630, which provides a suitable indication via a computer system to a display 632.

Figure 14F:
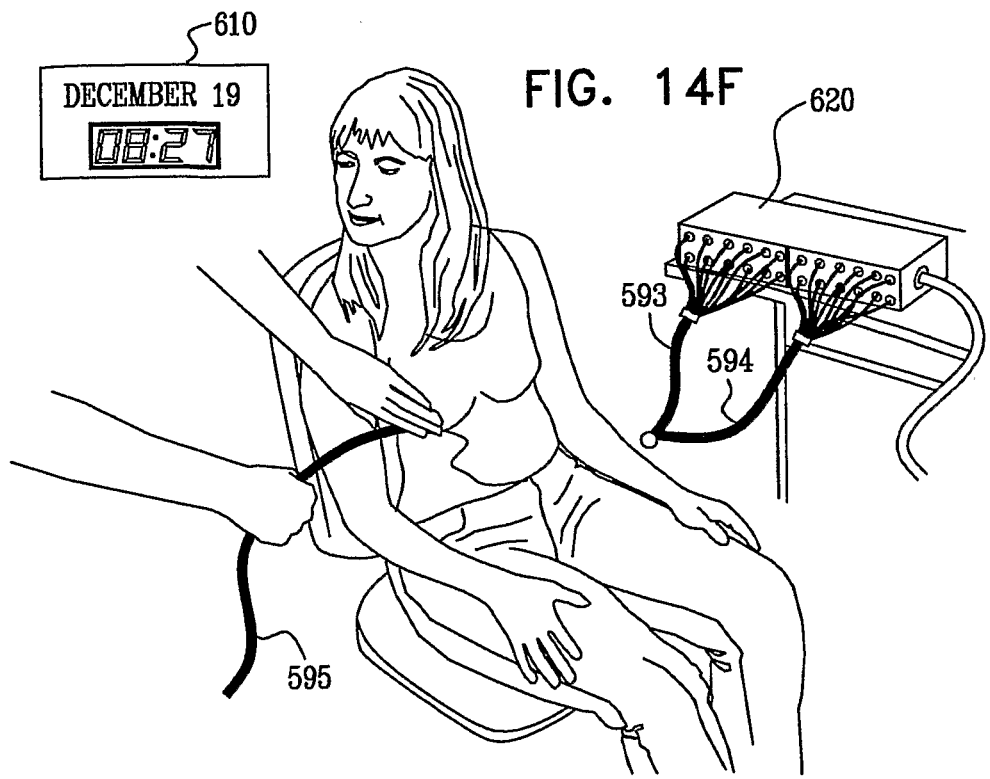
Figure 14G:
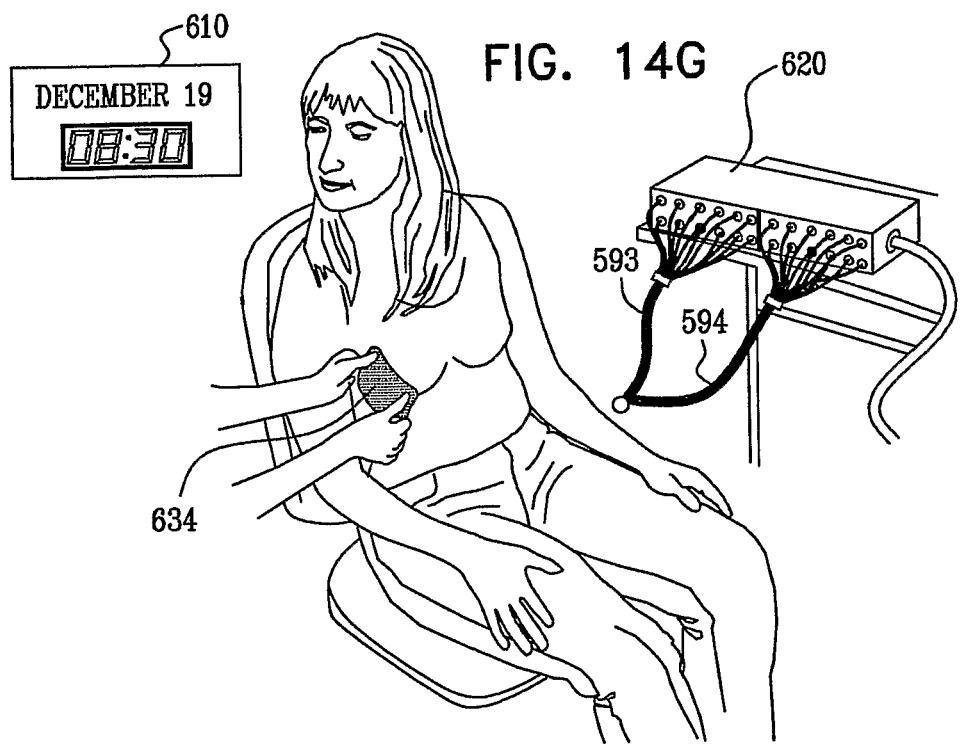

Immediately following completion of the radiation treatment, the bundle 595 of tubes 593 and 594 can be disconnected, as by pulling, from the reconstructive breast prosthesis 508 without requiring surgical intervention, as seen in FIG. 14F. The remaining incision can be left to heal naturally and is preferably covered by a bandage 634 as seen in FIG. 14G.

It is a particular feature of the present invention that highly location-specific radiation treatment can be provided over a relatively short time in a doctor's office environment, without necessitating a further surgical procedure. This is symbolically illustrated in FIGS. 14D-14G by the date and time clock 610.

Reference is now made to FIGS. 15A, 15B, 15C and 15D, which are, respectively, pictorial top view, pictorial bottom view, first sectional and second sectional illustrations of an integrally formed internal skeletal element 100' employed in an implantable tissue expander in accordance with a preferred embodiment of the present invention.

Figure 15A:
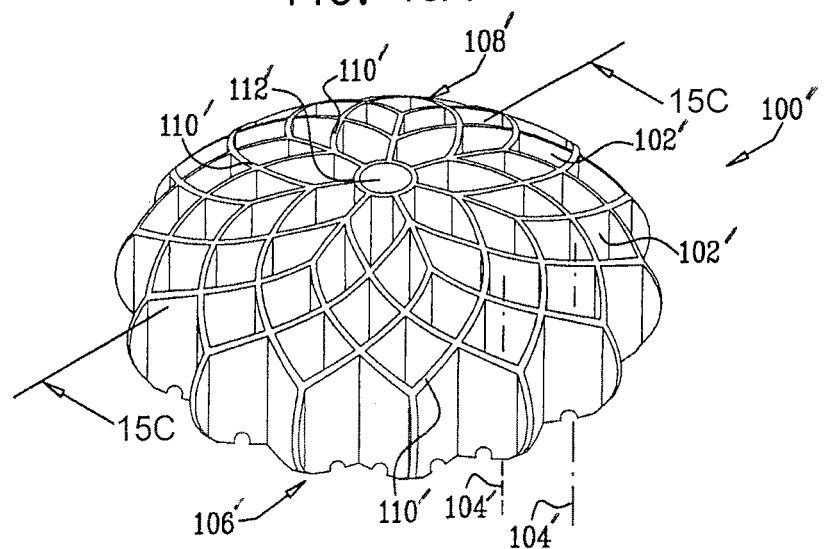
Figure 15B:
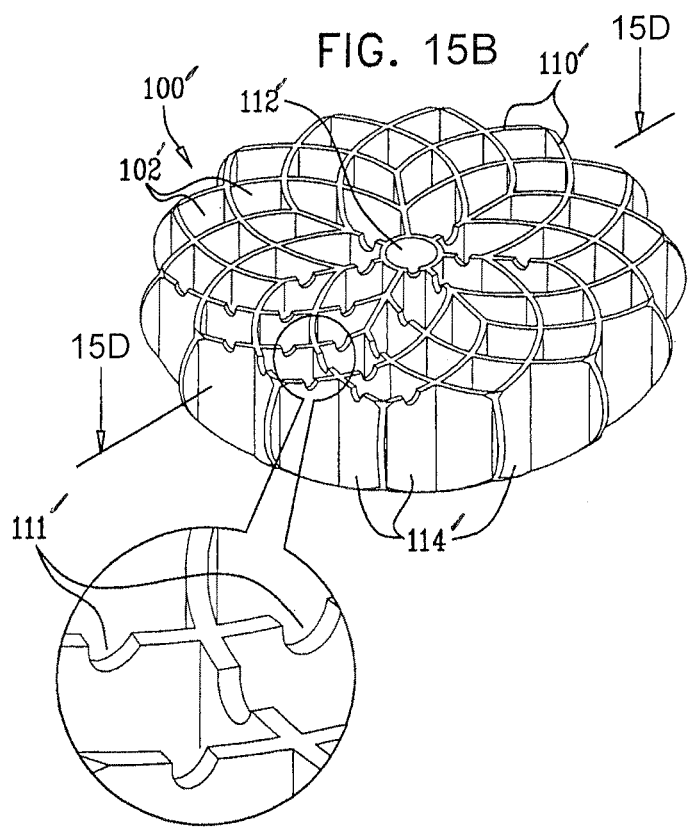
Figure 15C:
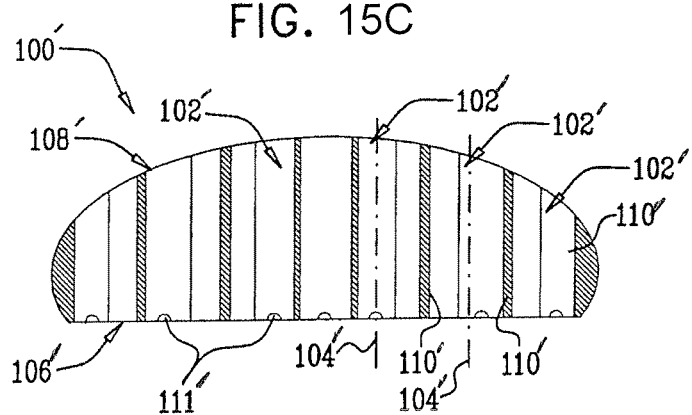
Figure 15D:
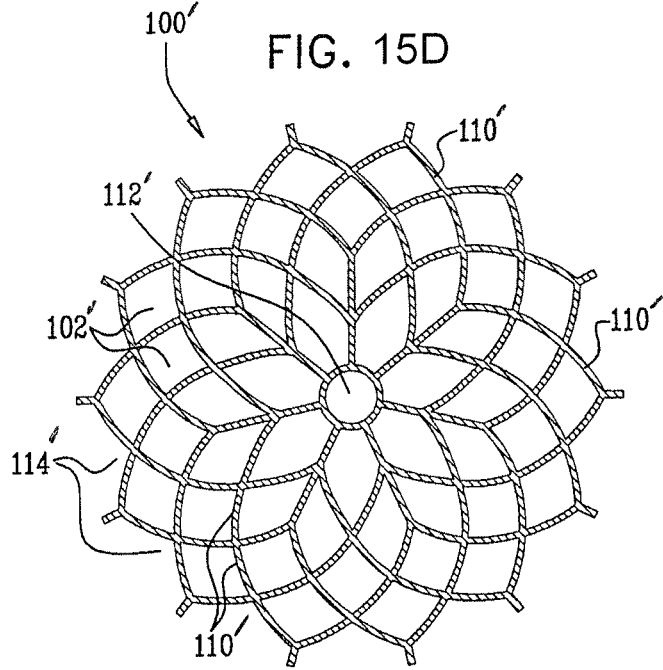
Figure 16A:
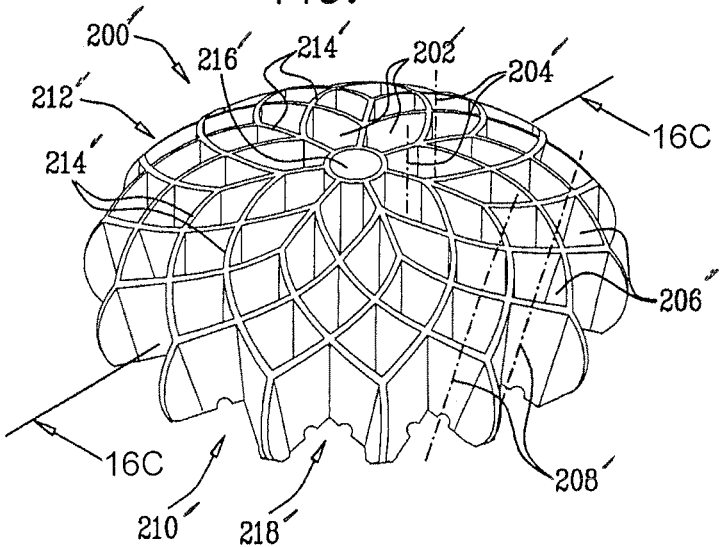
Figure 16B:
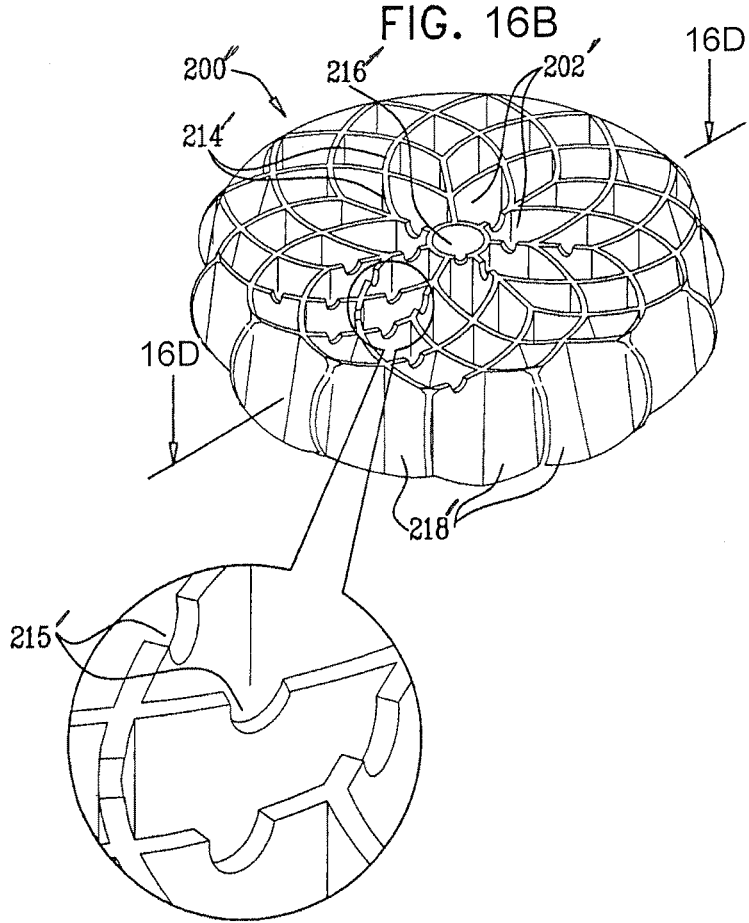
Figure 16C:
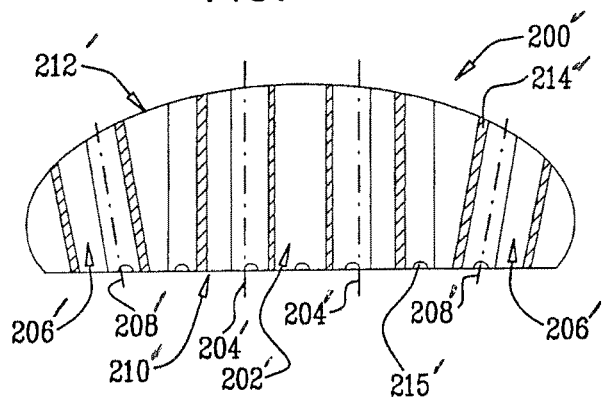
Figure 16D:
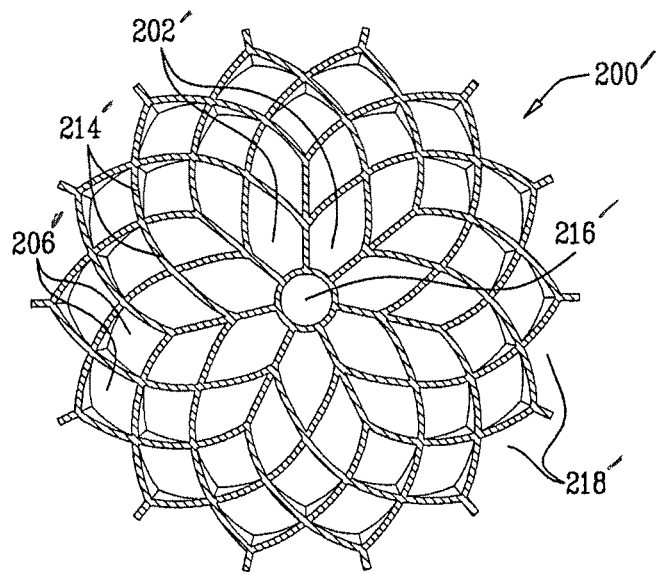

As seen in FIGS. 15A-15D, the integrally formed internal skeletal element 100' includes an array of elongate cells 102' extending along mutually generally parallel axes 104' from an imaginary base surface 106', which is typically flat, as in the illustrated embodiment, to an imaginary outer surface 108', which is preferably generally convex and is tucked in adjacent the imaginary base surface 106' as seen clearly in FIGS. 15A-15C. Elongate cells 102' are mutually defined by elongate cell walls 110' formed of a resilient material. Elongate cell walls 110' are preferably formed so as to define fluid passageways 111' communicating between adjacent cells 102'.

In the illustrated embodiment, the array of elongate cells 102' is preferably characterized in that it includes a central cylindrical cell 112' and that elongate cell walls 110' are of generally uniform thickness. It is also characterized in that a regular pattern of partial cells 114' are located along the periphery of the array. In the illustrated embodiment of FIGS. 15A-15D, all of the partial cells 114' are identical. In other embodiments, this is not necessarily the case. Alternatively, the elongate well walls 110' need not be of generally uniform thickness and may be of different thicknesses and/or varying thickness.

Reference is now made to FIGS. 16A, 16B, 16C and 16D, which are respectively pictorial top view, pictorial bottom view, first sectional and second sectional illustrations of an integrally formed internal skeletal element 200' employed in an implantable tissue expander in accordance with a preferred embodiment of the present invention.

As seen in FIGS. 16A-16D, the integrally formed internal skeletal element 200' includes an array of elongate cells including a first plurality of elongate cells 202' at the center of the array, which cells 202' extend along mutually generally parallel axes 204' and a second plurality of elongate cells 206', each of which extends along an axis 208' which is splayed outwardly with respect to axes 204'. Cells 202' and 206' extend from an imaginary base surface 210', which is typically flat, as in the illustrated embodiment, to an imaginary outer surface 212', which is preferably generally convex and is tucked in adjacent the imaginary base surface 210' as seen in FIGS. 16A-16D. Elongate cells 202' and 206' are mutually defined by elongate cell walls 214' formed of a resilient material. Elongate cell walls 214' are preferably formed so as to define fluid passageways 215' communicating between adjacent cells 202' and 206'.

In the illustrated embodiment, the array of elongate cells 202' is preferably characterized in that it includes a central cylindrical cell 216' and that elongate cell walls 214' are of generally uniform thickness. It is also characterized in that a regular pattern of partial cells 218' are located along the periphery of the array. In the illustrated embodiment of FIGS. 16A-16D, all of the partial cells 218' are identical. In other embodiments, this is not necessarily the case.

Reference is now made to FIGS. 17A, 17B, 17C and 17D, which are respectively pictorial top view, pictorial bottom view, first sectional and second sectional illustrations of an integrally formed internal skeletal element 300' employed in an implantable tissue expander in accordance with a preferred embodiment of the present invention.

Figure 17A:
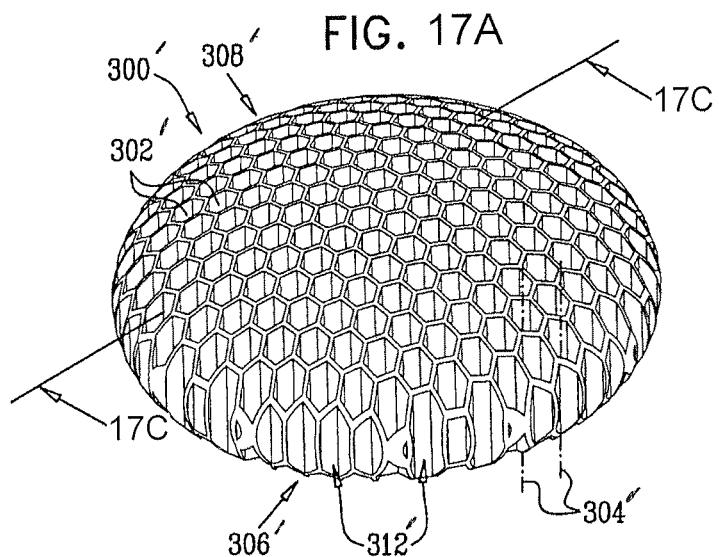
Figure 17B:
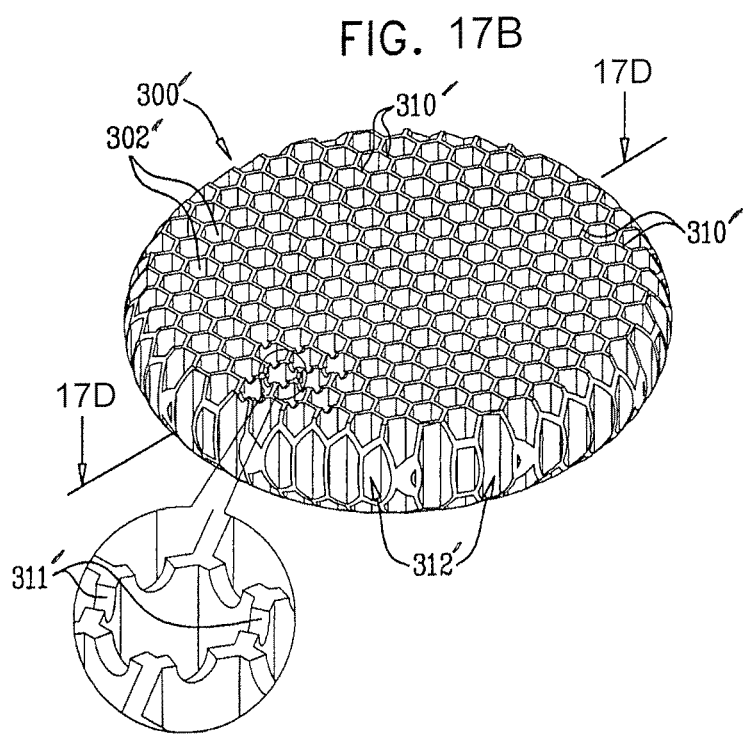
Figure 17C:
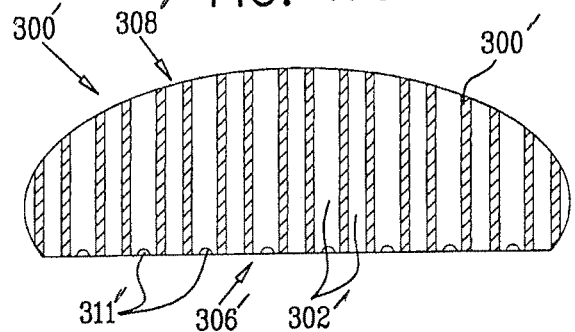
Figure 17D:
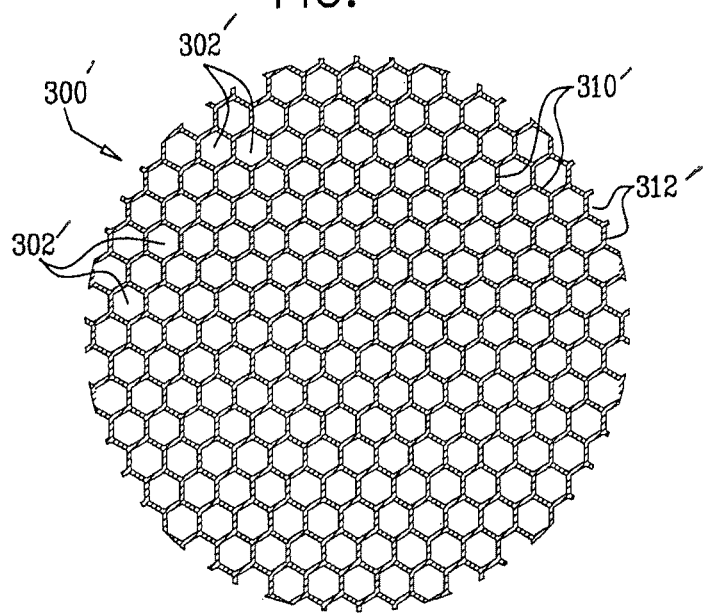

As seen in FIGS. 17A-17D, the integrally formed internal skeletal element 300' includes an array of identical elongate cells 302', each having an hexagonal cross section, extending along mutually generally parallel axes 304' from an imaginary base surface 306', which is typically flat, as in the illustrated embodiment, to an imaginary outer surface 308', which is preferably generally convex and is tucked in adjacent the imaginary base surface 306' as seen clearly in FIGS. 17A-17C. Elongate cells 302' are mutually defined by elongate cell walls 310' formed of a resilient material. Elongate cell walls 310' are preferably formed so as to define fluid passageways 311' communicating between adjacent cells 302'.

In the illustrated embodiment, the array of elongate cells 302' is preferably characterized in that elongate cell walls 310' are of generally uniform thickness. It is also characterized in that a regular pattern of partial cells 312' are located along the periphery of the array. In the illustrated embodiment of FIGS. 17A-17D, the partial cells 312' are not identical.

It will be appreciated by persons skilled in the art that the present invention is not limited to what has been. particularly shown and described hereinabove. Rather the scope of the invention includes both combinations and subcombinations of the various features described hereinabove as well as modifications and variations thereof which would occur to persons skilled in the art upon reading the foregoing description and which are not in the prior art.

The invention claimed is:

1. A reconstructive breast prosthesis suitable for implantation into a void in a breast following a lumpectomy procedure in which a body of tissue is excised from the breast, the reconstructive breast prosthesis comprising:
    an implant body defined by an outer wall configured to contact a breast tissue surrounding the prosthesis following implantation thereof and enclosing a volume, said volume being the entire interior of said prosthesis, said interior being non-liquid filled, said implant body is at least generally configured to assume an implant shape corresponding to the shape of the body of tissue excised from the breast; and
    implant shape retaining structures configured to maintain said implant body in said implant shape, said shape retaining structures comprising:
        (i) a first shape retaining structure configured to resist collapse, comprising a rib extending between opposing inner surface regions of said implant body and spanning the entire area between said opposing inner surface regions; and
        (ii) a second shape retaining structure in the form of at least one nonstretchable resilient mesh configured to prevent undesired expansion by defining a fixed surface area of said implant body,
    said reconstructive breast prosthesis having an overall density which is at least one of: less than the density of the body of tissue excised from the breast, less than the density of the remaining tissue of the breast surrounding the implant body and less than 0.5 grams/cc.

2. The reconstructive breast prosthesis of claim 1, wherein said reconstructive breast prosthesis has a specific gravity which is less than 0.9 gm/cm3.

3. The reconstructive breast prosthesis of claim 1, wherein said reconstructive breast prosthesis has a specific gravity which is less than 0.5 gm/cm3.

4. The reconstructive breast prosthesis of claim 1, wherein said implant body is formed of a resilient biocompatible material.

5. The reconstructive breast prosthesis of claim 1, wherein said first shape retaining structure includes at least one spring.

6. The reconstructive breast prosthesis of claim 1, further comprising at least one tube which is in communication with an interior of said implant body.

7. The reconstructive breast prosthesis of claim 6, wherein said implant body comprises at least two mutually sealed portions.

8. The reconstructive breast prosthesis of claim 7, wherein said at least one tube includes at least two tubes, each communicating with one of said at least two mutually sealed portions.

9. The reconstructive breast prosthesis of claim 8, wherein at least one of said at least two tubes is selectably detachable from a corresponding one of said at least two mutually sealed portions.

10. The reconstructive breast prosthesis of claim 8, further comprising at least one valve governing communication between at least one of said at least two tubes and a corresponding at least one of said at least two mutually sealed portions.

11. The reconstructive breast prosthesis of claim 1, further comprising at least one pump in fluid communication with an interior of said implant body.

12. The reconstructive breast prosthesis of claim 1, further comprising at least one injection port.

13. The reconstructive breast prosthesis of claim 12, said at least one injection port comprises first and second mutually opposed injection ports.

14. The reconstructive breast prosthesis of claim 1, further comprising an internal skeletal element extending between a base surface and an outer surface and including at least one plurality of elongate cells extending along mutually generally parallel axes from the base surface to the outer surface and being defined by elongate cell walls formed of a resilient material.

15. The reconstructive breast prosthesis of claim 1, wherein said first shape retaining structure includes mutually perpendicular interior ribs, each extending between opposing inner surfaces regions of the implant body and spanning the entire area between said opposing inner surface regions.

16. A method for implantation of a reconstructive breast prosthesis into a void in a breast following a lumpectomy procedure in which a body of tissue is excised from the breast through an incision, the method comprising:
    inserting said reconstructive breast prosthesis into said void, said reconstructive breast prosthesis including an implant body defined by an outer wall configured to contact a breast tissue surrounding the prosthesis following implantation thereof and enclosing a volume, said volume being the interior of said prosthesis, said interior being non-liquid filled, said implant body is at least generally configured to assume an implant shape corresponding to the shape of the body of tissue excised from the breast, and implant shape retaining structures configured to maintain said implant body in said implant shape, said shape retaining structures comprising:
        (i) a first shape retaining structure configured to resist collapse, comprising at least one rib extending between opposing inner surface regions of said implant body and spanning the entire area between said opposing inner surface regions; and
        (ii) a second shape retaining structure in the form of at least one non-stretchable resilient mesh configured to prevent undesired expansion by defining a fixed surface area of said implant body, said reconstructive breast prosthesis having an overall density which is at least one of: less than the density of the body of tissue excised from the breast; or less than the density of the remaining tissue of the breast surrounding the implant body; and
    closing said incision.

* * * * *